United States Patent [19]

Beutler et al.

[11] Patent Number: 5,234,811
[45] Date of Patent: Aug. 10, 1993

[54] ASSAY FOR A NEW GAUCHER DISEASE MUTATION

[75] Inventors: Ernest Beutler, La Jolla; Joseph A. Sorge, Rancho Santa Fe, both of Calif.

[73] Assignee: The Scripps Research Institute, La Jolla, Calif.

[21] Appl. No.: 767,135

[22] Filed: Sep. 27, 1991

[51] Int. Cl.$^5$ .................. C12Q 1/68; C07H 15/12
[52] U.S. Cl. .................. 435/6; 435/91; 935/77; 935/78; 536/23.1
[58] Field of Search .................. 435/6, 91; 436/501, 436/94; 935/77, 78

[56] References Cited
PUBLICATIONS

Beutler, et al., "The Facile Detection of the nt 1226 Mutation of Glucocerebrosidase by 'Mismatched' PCR", *Clin. Chim. Acta.*, 194:161–166 (1990).

Dahl, et al., "Gaucher Disease Type III (Norrbottnian Type) is Caused by a Single Mutation in Exon 10 of the Glucocerebrosidase Gene", *Am. J. Hum. Genet.*, 47:275–279 (1990).

Hong, et al., "Sequence of Two Alleles Responsible for Gaucher Disease", *DNA and Cell biol.*, 9:233–241 (1990).

Horowitz, et al., "The Human Glucocerebrosidase Gene and Pseudogene: Structure and Evolution", *Genomics*, 4:87–96 (1989).

Kumar, et al., "Designed Diagnostic Restriction Fragment Length, Polymorphisms for the Detection of Point Mutations in ras Oncogenes", *Oncogene Res.*, 1:235–241 (1989).

Latham, et al., "Heterogeneity of Mutations in the Acid β-Glucosidase Gene of Gaucher Disease Patients", *DNA Cell Biol.*, 10:15–21 (1991).

Sorge, et al., "Molecular Cloning and Nucleotide Sequence of Human Glucocerebrosidase cDNA", *PNAS, USA*, 82:7289–7293 (1985).

Sorge, et al., "The Human Glucocerebrosidase Gene Has Two Functional ATG Initiator Condons", *Am. J. Hum. Genet.*, 41:1016–1024 (1987).

Sorge, et al., "High Level Transcription of the Glucocerebrosidase Pseudogene in Normal Subjects and Patients with Gaucher Disease", *J. Clin. Invest.*, 86:1137–1141 (1990).

Theophilus, et al., "Gaucher Diasese: Molecular Heterogeneity and Phenotype–Genotype Correlations", *Am. J. Hum. Genet.*, 45:212–225 (1989).

Tsuji, et al., "A Mutation in the Human Glucocerebrosidase Gene in Neuronopathic Gaucher's Disease", *New Engl. J. Med.*, 316:570–575 (1987).

Tsuji, et al., "Genetic Heterogeneity in Type 1 Gaucher Disease: Multiple Genotypes in Ashkenazic and Non-Ashkenazic Individuals", *PNAS, USA*, 85:2349–2352 (1988).

Zimran, et al., "Prediction of Severity of Gaucher's Disease by Identification of Mutations at DNA Level", *The Lancet*, 2:349–352 (1989).

Zimran, et al., "A Glucocerebrosidase Fusion Gene in Gaucher Disease", *J. Clin. Invest.*, 85:219–222 (1990).

Primary Examiner—Stephanie W. Zitomer
Attorney, Agent, or Firm—Douglas A. Bingham; Thomas Fitting; April C. Logan

[57] ABSTRACT

A method for detecting a new Gaucher disease mutation in an allele in a human having an insertion mutation of a guanine nucleotide adjacent to nucleotide position 57 in the normal glucocerebrosidase gene exon 2 is provided. Identification of the mutation is accomplished by first amplifying, with a polymerase chain reaction (PCR) primer, a region of human genomic DNA containing nucleotide positions 57 and 58 of glucocerebrosidase gene exon 2 followed by detection of the mutation.

28 Claims, No Drawings

ASSAY FOR A NEW GAUCHER DISEASE MUTATION

This invention was made with the support of the United States Government, and the United States Government has certain rights in the invention pursuant to the National Institutes of Health Contracts DK36639 and RR00833.

TECHNICAL FIELD

The present invention relates to a method for detecting a Gaucher disease allele in a human having an insertion mutation of a guanine nucleotide adjacent to nucleotide position 57 in the normal glucocerebrosidase gene exon 2.

BACKGROUND OF THE INVENTION

Gaucher disease is an autosomal recessive disorder caused by a deficiency of glucocerebrosidase, the enzyme that is required for the lysosomal degradation of lipids containing covalently bound sugars (glycolipids). Brady et al., *J. Biol. Chem.*, 240:39–43 (1965). In the absence of glucocerebrosidase, the extremely insoluble glucosylceramide (glucocerebroside) accumulates.

The gene for glucocerebrosidase is located on chromosome-1 in the region of q21. See, Shafit-Zagardo et al., *Am. J. Hum Genet.*, 33:564-575 (1981); Ginns et al., *Proc. Natl. Acad. Sci., U.S.A.*, 82:7101-7105 (1985). The fact that a number of different mutations caused Gaucher disease was inferred from clinical observations (Beutler, *Genetic Diseases Among Ashkenazi Jews*, eds. Boudman et al., Raven Press, NY, pp. 157–169 (1979)) and from differences in the kinetic properties of the residual enzyme in different patients with the disorder. Grabowski et al., *Am. J. Hum. Genet.*, 37:499–510 (1985). However, real understanding of the genetics of this disease has had to await the cloning and sequencing of the cDNA (Sorge et al., *Proc. Natl. Acad. Sci., U.S.A.*, 82:7289-7293 (1985) and Tsuji et al., *N. Engl. J. Med.*, 316:570–621 (1987)) and of the gene (Horowitz et al., *Genomics*, 4:87–96 (1989)). Analysis of mutations is complicated by the existence of a pseudogene which is approximately 16 kilobases (Kb) downstream from the glucocerebrosidase gene. Zimran et al., *J. Clin. Invest.*, 86:1137–1141 (1990). The pseudogene is about 95% homologous to the functional gene. It is transcribed (Sorge et al., *J. Clin. Invest.*, 86:1137-1141 (1990)), but cannot be translated into glucocerebrosidase because of numerous deletions of coding sequences.

Point mutations that cause Gaucher disease have been summarized recently. Latham et al., *DNA Cell Biol.*, 10:15-21 (1991) and Grabowski et al., *CRC Crit. Rev. Biochem. Mol. Biol.*, 25:385–414 (1990). In addition, fusion genes in which the 5' sequence is that of the active gene and the 3' sequence that of the pseudogene have been documented See, Zimran et al., *J. Clin. Invest.*, 85:219-222 (1990); Latham et al., *DNA Cell Biol.*, 10:15-21 (1991); Eyal et al., *Gene*, 96:277-283 (1990). When investigated at the genomic level, at least some such fusion genes appear to be the result of unequal crossing-over with loss of the portion of the gene between the gene and pseudogene. Zimran et al., *J. Clin. Invest.*, 85:219-222 (1990).

The disease is most prevalent in the Jewish population with a heterozygote frequency that has been estimated to approach 9%. Zimran et al., *Am. J. Hum. Genet.*, (1991). In Jewish patients with clinically significant Gaucher disease, about 75% of the disease-causing alleles contain a characteristic adenine to guanine (A→G) mutation at cDNA nucleotide position (nt) 1226 (designated the 1226G mutation) which is in the codon coding for amino acid residue 370 of the mature protein. See, Tsuji et al., *Proc. Natl. Acad. Sci., U.S.A.*, 85:2349-2352, 5708 (1988); Zimran et al., *Lancet*, 2:349-352 (1989). The corresponding position of the mutation in the glucocerebrosidase gene is in exon 9 at nucleotide position 2. The same mutation is also common in the non-Jewish population, where it is found to account for approximately 25% of the disease-producing alleles. This mutation is always found in a gene that also contains a characteristic RFLP (restriction fragment length polymorphisms) with the enzyme Pvu II at genomic nt 3931, suggesting that the mutation may have occurred only once. Zimran et al., *Am J. Hum. Genet.*, 46:902-905 (1990).

A second, much less common mutation is at cDNA nucleotide position 1448 where cytosine has been substituted for thymine (T→C). See, Tsuji et al., *N. Engl. J. Med.*, 316:570-621 (1987); Dahl et al., *Am. J. Hum. Genet.* 47:275-278 (1990). The corresponding position of the mutation in the functional glucocerebrosidase gene is in exon 10 at nucleotide position 60. The 1448C mutation accounts for only about 2% of Jewish Gaucher disease producing alleles and for about 40% of the alleles in non-Jewish patients. Thus, in both Jewish and non-Jewish patients many of the Gaucher disease alleles have remained unidentified and have been designated "?".

The T→C point mutation in the functional glucocerebrosidase gene exactly matches the sequence found normally in the glucocerebrosidase pseudogene cDNA. See Horowitz et al., *Genomics*, 4:87-96 (1989), Tsuji et al., supra, and Sorge et al., *Proc. Natl. Acad. Sci., U.S.A.*, 82:7289-7293 (1985). In addition, the presence of the T→C point mutation in exon 10 has been identified in a fusion gene which was the result of rearrangement of DNA in the glucocerebrosidase gene complex. See, Zimran et al., *J. Clin. Invest.*, 85:219-222 (1990). The fusion gene resulted from an unequal cross-over event between the functional glucocerebrosidase gene and the pseudogene.

In this particular fusion gene, the 5' end of the transcribed cDNA was the functional gene and the 3' end was the pseudogene. The cross-over event occurred 5' or upstream to exon 10. Thus, the region of the pseudogene containing the cysteine nucleotide corresponding to the point mutation in the functional gene is in the 3' region of the fusion gene. In this situation, the nucleotide position of the cystein nucleotide would not alter. However, if an unequal cross-over event occurs sufficiently 5' to the mutation, the nucleotide position of the mutation in exon 10 may change. Therefore, the designation of nucleotide position 60 in exon 10 corresponding to nucleotide position 1448 in the cDNA would no longer be accurate. However, the region surrounding the mutation would be found in the same context, i.e., the surrounding nucleotides would be the same.

Three clinical subtypes of Gaucher Disease have been delineated. See, Beutler, *Blood Rev.*, 2:59-70 (1988); Martin et al., *Adv. Pediatr.*, 36:277-306 (1989). Type I is by far the most common; more than 99% of Gaucher disease patients have type I disease. It is defined by the fact that there is no neurologic involvement. Type II disease is a fulminating disorder with severe neurologic manifestations and death within the first 18 months of life Type III, the juvenile form of the disorder is characterized by later onset of neurologic symptoms than type II disease and by a chronic course.

Although all body cells are deficient in glucocerebrosidase activity in Gaucher disease, it is the glycolipid engorged macrophages that are responsible for all of the non-neurologic disease manifestation. The liver and spleen are usually enlarged. Splenomegaly results in or contributes to thrombocytopenia. Hepatic involvement is often associated with fibrosis and with abnormal liver function tests. In some patients right-to-left pulmonary shunting occurs, presumably secondary to the liver disease. Direct involvement of the pulmonary parenchyma may also rarely occur. Schneider et al., *Am. J. Med.*, 63:475–480 (1977).

Bone involvement is common in Gaucher disease. Flaring of the distal femur, the so-called Erlenmeyer flask deformity, is a classical sign of the disease. Aseptic necrosis of the femoral heads, bone infarcts, and pathologic fractures of the long bone are all frequent complications of Gaucher disease. Stowens et al., *Medicine*, 64:310–322 (1985). Bone crises (Yosipovitch et al., *Isr. J. Med. Sci.*, 26:593–595 (1990)), episodes of pain and swelling, sometimes accompanied by fever but without X-ray changes are common, recurrent manifestations of the disease.

There are patients with Type I disease who experience minimal manifestations of the disorder or none at all. Often the diagnosis in patients with such very mild disease is made in middle or old age. The presence of Gaucher disease in such patients is often appreciated only when bone marrow examination is performed for some unrelated disorder or in the course of investigation of modest thrombocytopenia. On more careful examination slight splenomegaly is often detected and minimal stigmata of the disease may be apparent when skeletal X-rays are examined. Such patients usually need no treatment.

In type II disease, neurologic findings usually become manifest in the middle of the first year of life with the development of oculomotor apraxia, strabismus, hypertonicity and retroflexion of the head. Similar neurologic symptoms occurring in the first few years of life and occasionally even later characterize type III disease.

Determination of leukocyte β-glucoside activity is a reliable and simple way to diagnose Gaucher disease. Unfortunately, most patients with the disorder are still diagnosed by bone marrow examination. While this is understandable if the diagnosis was not suspected, it is an inappropriate and anachronistic procedure when Gaucher disease has been included in the differential diagnosis. Beutler and Savin, *Blood*, 76:646–648 (1990). Ancillary tests that are useful include the determination of the activity of serum acid phosphatase (Robinson et al., *Clin. Chem.*, 26:371–382 (1980)) and the angiotensin converting enzyme. Lieberman et al., *N. Engl. J. Med.*, 294:1442–1444 (1976). The levels of these enzymes, as well as levels of a number of lysosomal enzymes that are not usually measured in clinical laboratories, is increased in most but not all patients with Gaucher disease.

Recently, facile technology for the detection of the common mutations, such as those at nucleotide position 1226 (Beutler et al., *Clin Chim. Acta.*, 194:161–166 (1990)) and nucleotide position 1448 (Zimran et al., *Lancet*, 2:349–352 (1989)), have been developed using the polymerase chain reaction (PCR).

BRIEF SUMMARY OF THE INVENTION

The present invention relates to detecting a new Gaucher disease mutation which is characterized by an insertion mutation of a guanine nucleotide adjacent to nucleotide position 84 in glucocerebrosidase cDNA. The corresponding position of the mutation in the glucocerebrosidase gene is in exon 2 adjacent to nucleotide position 57.

Thus, in one embodiment, a human genetic screening method is contemplated. The method comprises assaying a nucleic acid sample isolated from a human for the presence of a glucocerebrosidase gene insertion mutation characterized as an insertion of a guanine nucleotide adjacent to nucleotide position 57 of glucocerebrosidase gene exon 2.

In a preferred embodiment, the method comprises treating, under amplification conditions, a sample of genomic DNA from a human with a polymerase chain reaction (PCR) primer pair for amplifying a region of human genomic DNA containing nucleotide positions 57 and 58 of glucocerebrosidase gene exon 2. The PCR treatment produces an amplification product containing the region, which is then assayed for the presence of a guanine (G) nucleotide insertion mutation adjacent to nucleotide position 57 of the exon.

One object of the present invention is to provide a method for screening for at least two, and preferably three, glucocerebrosidase gene mutations in a single nucleic acid sample. Such multiple screening is most advantageously performed by producing two PCR amplification products, one containing cDNA nucleotide (nt) 84, and one containing cDNA nt 1226 and/or cDNA nt 1448, or equivalent genomic DNA regions, in one PCR amplification. Thus, primers for amplifying (1) a region of genomic DNA containing nucleotide position 57 of glucocerebrosidase gene exon 2, and (2) a region of genomic DNA containing nucleotide position 2 of exon 9 and nucleotide position 60 of exon 10. The PCR amplification products are then assayed for the exon 2 nt 57G, exon 9 nt 2 A→G and exon 10 nt 60 T→C mutations.

DETAILED DESCRIPTION OF THE INVENTION

A. Definitions

| Code | Group | TABLE OF CORRESPONDENCE Nucleotide(s) |
|---|---|---|
| A | A | adenine |
| C | C | cytosine |
| G | G | guanine |
| T | T | thymine (in DNA) |
| U | U | uracil (in RNA) |
| Y | C or T(U) | pyrimidine |
| R | A or G | purine |
| M | A or C | amino |
| K | G or T(U) | keto |
| S | G or C | strong interaction (3 hydrogen bonds) |
| W | A or T(U) | weak interaction (2 hydrogen bonds) |
| H | A or C or T(U) | not-G |
| B | G or T(U) or C | not-A |
| V | G or C or A | not-T or not-U |
| D | G or A or T(U) | not-C |
| N | G,A,C or T(U) | any |

Allele: A variant of DNA sequence of a specific gene. In diploid cells a maximum of two alleles will be present, each in the same relative position or locus on homologous chromosomes of the chromosome set. When alleles at any one locus are identical the individual is said to be homozygous for that locus, when they differ the individual is said to be heterozygous for that locus. Since different alleles of any one gene may vary by only a single base, the possible number of alleles for any one gene is very large. When alleles differ, one is often dominant to the other, which is said to be recessive. Dominance is a property of the phenotype and does not imply inactivation of the recessive allele by the dominant. In numerous examples the normally functioning (wild-type) allele is dominant to all mutant alleles of more or less defective function. In such cases the general explanation is that one functional allele out of two is sufficient to produce enough active gene product to support normal development of the organism (i.e., there is normally a two-fold safety margin in quantity of gene product).

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule In RNA, uracil (U) is substituted for thymine.

Nucleic Acid: A polymer of nucleotides, either single or double stranded.

Polynucleotide: A polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA.

Duplex DNA: a double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it nonrandomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analog: A purine or pyrimidine nucleotide that differs structurally from A, T, G, C, or U, but is sufficiently similar to substitute for the normal nucleotide in a nucleic acid molecule.

DNA Homolog: Is a nucleic acid having a preselected conserved nucleotide sequence and a sequence coding for a receptor capable of binding a preselected ligand.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Stop Codon: Any of three codons that do not code for an amino acid, but instead cause termination of protein synthesis. They are UAG, UAA and UGA and are also referred to as a nonsense or termination codon.

Leader Polypeptide: A short length of amino acid sequence at the amino end of a protein, which carries or directs the protein through the inner membrane and so ensures its eventual secretion into the periplasmic space and perhaps beyond. The leader sequence peptide is commonly removed before the protein becomes active.

Reading Frame: Particular sequence of contiguous nucleotide triplets (codons) employed in translation. The reading frame depends on the location of the translation initiation codon.

B. Methods

The present invention provides a novel method for screening humans for glucocerebrosidase alleles associated with Gauchers disease. The invention was born out of the discovery that Gaucher disease can be caused by an insertion mutation in the glucocerebrosidase gene DNA sequence adjacent nucleotide position 57 of exon 2. That is, a guanine is inserted adjacent to the guanine normally present at nucleotide position 57 of normal exon 2. Another way of expressing this is that nucleotide position 57 (nt 57) of exon 2 is occupied by one or two nucleotides. In the normal (wild type) gene, nt 57 is occupied by a single guanine, and in the newly discovered mutant gene, nt 57 is occupied by two guanines. The mutation at nt 57 (i.e., insertion adjacent to nt 57) sometimes referred to herein as nt 57G or cDNA 84GG.

The assay method can be used to diagnose either the disease itself or a heterozygous carrier state. Generally, the method involves preparing a nucleic acid sample for screening and then assaying the sample for one or more of the Gaucher disease alleles.

A glucocerebrosidase gene is a nucleic acid whose nucleotide sequence codes for glucocerebrosidase or mutant glucocerebrosidase. It can be in the form of genomic DNA, an mRNA or cDNA, and in single or double stranded form. Preferably, genomic DNA is used because of its relative stability in biological samples compared to mRNA. The sense strand of the complete genomic sequence of the normal wild type) glucocerebrosidase gene is listed in the Sequence Listing as SEQ ID NO 1. The gene is comprised of eleven exons and ten introns, the nucleotide positions of which are indicated in the features of SEQ ID NO 1.

The nucleic acid sample is obtained from cells, typically peripheral blood leukocytes.

Where mRNA is used, the cells will be lysed under RNase inhibiting conditions. In one embodiment, the first step is to isolate the total cellular mRNA. Poly A+ mRNA can then be selected by hybridization to an oligo-dT cellulose column.

In preferred embodiments, the nucleic acid sample is enriched for a presence of glucocerebrosidase allelic material. Enrichment is typically accomplished by subjecting the genomic DNA or mRNA to a primer extension reaction employing a polynucleotide synthesis primer as described herein. Particularly preferred methods for producing a sample to be assayed use preselected polynucleotides as primers in a polymerase chain reaction (PCR) to form an amplified (PCR) product.

(1) Preparation of Polynucleotide Primers

The term "polynucleotide" as used herein in reference to primers, probes and nucleic acid fragments or segments to be synthesized by primer extension is defined as a molecule comprised of two or more deoxyribonucleotides or ribonucleotides, preferably more than 3. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg et al., *Nucl. Acids Res.*, 12:7057-70 (1984); Studier et al., *J. Mol. Biol.*, 189:113-130 (1986); and *Molecular Cloning: A Laboratory Manual*, Second Edition, Maniatis et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi et al., *Biotechnology*, 6:1197-1202 (1988). RNA-directed polymerases produce large numbers of RNA strands from a small number of template RNA strands that contain a template sequence or replication initiation site. These polymerases typically give a one million-fold amplification of the template strand as has been described by Kramer et al., *J. Mol. Biol.*, 89:719-736 (1974).

The polynucleotide primers can be prepared using any suitable method, such as, for example, the phosphotriester or phosphodiester methods see Narang et al., *Meth. Enzymol.*, 68:90, (1979); U.S. Pat. Nos. 4,356,270, 4,458,066, 4,416,988, 4,293,652; and Brown et al., *Meth. Enzymol.*, 68:109, (1979).

The choice of a primer's nucleotide sequence depends on factors such as the distance on the nucleic acid from the hybridization point to the region coding for the mutation to be detected, its hybridization site on the nucleic acid relative to any second primer to be used, and the like.

If the nucleic acid sample is to be enriched for glucocerebrosidase gene material by PCR amplification, two primers, i.e., a PCR primer pair, must be used for each coding strand of nucleic acid to be amplified. The first primer becomes part of the non-coding (antisense or minus or complementary) strand and hybridizes to a nucleotide sequence on the plus or coding strand. Second primers become part of the coding (sense or plus) strand and hybridize to a nucleotide sequence on the minus strand. One or both of the first and second primers can contain a nucleotide sequence defining an endonuclease recognition site. The site can be heterologous to the glucocerebrosidase gene being amplified.

In one embodiment, the present invention utilizes a set of polynucleotides that form primers having a priming region located at the 3'-terminus of the primer. The priming region is typically the 3'-most (3'-terminal) 15 to 30 nucleotide bases. The 3'-terminal priming portion of each primer is capable of acting as a primer to catalyze nucleic acid synthesis, i.e., initiate a primer extension reaction off its 3' terminus. One or both of the primers can additionally contain a 5'-terminal (5'-most) non-priming portion, i.e., a region that does not participate in hybridization to the preferred template.

In PCR, each primer works in combination with a second primer to amplify a target nucleic acid sequence. The choice of PCR primer pairs for use in PCR is governed by considerations as discussed herein for producing glucocerebrosidase gene regions. Useful priming sequences are shown in Table 2 and also in Examples 1B and 1D.

(2) Polymerase Chain Reaction

Glucocerebrosidase genes are comprised of polynucleotide coding strands, such as mRNA and/or the sense strand of genomic DNA. If the genetic material to be assayed is in the form of double stranded genomic DNA, it is usually first denatured, typically by melting, into single strands. The nucleic acid is subjected to a PCR reaction by treating (contacting) the sample with a PCR primer pair, each member of the pair having a preselected nucleotide sequence. The PCR primer pair is capable of initiating primer extension reactions by hybridizing to nucleotide sequences, preferably at least about 10 nucleotides in length, more preferably at least about 20 nucleotides in length and most preferably 17 nucleotides in length, conserved within the glucocerebrosidase alleles. The first primer of a PCR primer pair is sometimes referred to herein as the "sense primer" because it hybridizes to the coding or sense strand of a nucleic acid. In addition, the second primer of a PCR primer pair is sometimes referred to herein as the "anti-sense primer" because it hybridizes to a non-coding or anti-sense strand of a nucleic acid, i.e., a strand complementary to a coding strand.

The PCR reaction is performed by mixing the PCR primer pair, preferably a predetermined amount thereof, with the nucleic acids of the sample, preferably a predetermined amount thereof, in a PCR buffer to form a PCR reaction admixture. The admixture is thermocycled for a number of cycles, which is typically predetermined, sufficient for the formation of a PCR reaction product, thereby enriching the sample to be assayed for glucocerebrosidase genetic material.

PCR is typically carried out by thermocycling i.e., repeatedly increasing and decreasing the temperature of a PCR reaction admixture within a temperature range whose lower limit is about 30° C. to about 55° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined for assaying for mutations.

The PCR reaction is performed using any suitable method. Generally it occurs in a buffered aqueous solution, i.e., a PCR buffer, preferably at a pH of 7-9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C.–100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. Thus, for example, if DNA polymerase is used as inducing agent, the temperature is generally no greater than about 40° C. The thermocycling is repeated until the desired amount of PCR product is produced. An exemplary PCR buffer comprises the following: 50 mM KCl; 10 mM Tris-HCl; pH 8.3; 1.5 mM $MgCl_2$; 0.001% (wt/vol) gelatin, 200 μM dATP; 200 μM dTTP; 200 μM dCTP; 200 μM dGTP; and 2.5 units Thermus aquaticus DNA polymerase I (U.S. Pat. No. 4,889,818) per 100 microliters of buffer.

The inducing agent may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn over rate of the RNA polymerase amplifies the starting polynucleotide as has been described by Chamberlin et al., The Enzymes, ed. P. Boyer, PP. 87-108, Academic Press, New York (1982). Amplification systems based on transcription have been described by Gingeras et al., in PCR Protocols, A Guide to Methods and Applications, pp. 245-252, Academic Press, Inc., San Diego, Calif. (1990).

If the inducing agent is a DNA-dependent RNA polymerase and therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

The PCR reaction can advantageously be used to incorporate into the product a preselected restriction site useful in detecting a mutation in the glucocerebrosidase gene.

PCR amplification methods are described in detail in U.S. Pat. Nos. 4,683,192, 4,683,202, 4,800,159, and 4,965,188, and at least in several texts including "PCR Technology: Principles and Applications for DNA Amplification", H. Erlich, ed., Stockton Press, New York (1989); and "PCR Protocols: A Guide to Methods and Applications", Innis et al., eds., Academic Press, San Diego, Calif. (1990).

In preferred embodiments two pairs of first and second primers are used per amplification reaction. The amplification reaction products obtained from a plurality of different amplifications, each using a plurality of different primer pairs, can be combined or assayed separately.

However, the present invention also contemplates amplification using only one pair of first and second primers, and multiplex amplification (using up to about 8, 9 or 10 primer pairs).

(3) Nucleic Acid Sequence Analysis

Nucleic acid sequence analysis is approached by a combination of (a) physiochemical techniques, based on the hybridization or denaturation of a probe strand plus its complementary target, and (b) enzymatic reactions with endonucleases, ligases, and polymerases Nucleic acid can be assayed at the DNA or RNA level. The former analyzes the genetic potential of individual humans and the later the expressed information of particular cells.

In assays using nucleic acid hybridization, detecting the presence of a DNA duplex in a process of the present invention can be accomplished by a variety of means.

In one approach for detecting the presence of a DNA duplex, an oligonucleotide that is hybridized in the DNA duplex includes a label or indicating group that will render the duplex detectable. Typically such labels include radioactive atoms, chemically modified nucleotide bases, and the like.

The oligonucleotide can be labeled, i.e., operatively linked to an indicating means or group, and used to detect the presence of a specific nucleotide sequence in a target template Radioactive elements operatively linked to or present as part of an oligonucleotide probe (labeled oligonucleotide) provide a useful means to facilitate the detection of a DNA duplex. A typical radioactive element is one that produces beta ray emissions. Elements that emit beta rays, such as $^3H$, $^{12}C$, $^{32}P$ and $^{35}S$ represent a class of beta ray emission-producing radioactive element labels. A radioactive polynucleotide probe is typically prepared by enzymatic incorporation of radioactively labeled nucleotides into a nucleic acid using DNA kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate forming compound such as an EDTA-analogue so that a fluorescent lanthanide complex is formed. See U.S. Pat. No. 4,374,120, No. 4,569,790 and published Patent Application Nos. EP0139675 and WO87/02708.

Biotin or acridine ester-labeled oligonucleotides and their use to label polynucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a DNA duplex renders the duplex itself labeled and therefore distinguishable over other nucleic acids present in a sample to be assayed. Detecting the presence of the label in the duplex and thereby the presence of the duplex, typically involves separating the DNA duplex from any labeled oligonucleotide probe that is not hybridized to a DNA duplex.

Techniques for the separation of single stranded oligonucleotide, such as non-hybridized labeled oligonucleotide probe, from DNA duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the DNA duplex that is bound to an insoluble matrix. Exemplary is the Southern blot technique, in which the matrix is a nitrocellulose sheet and the label is 32P. Southern, *J. Mol. Biol.*, 98:503 (1975).

The oligonucleotides can also be advantageously linked, typically at or near their 5'-terminus, to a solid matrix, i.e., aqueous insoluble solid support. Useful solid matrices are well known in the art and include cross-linked dextran such as that available under the tradename SEPHADEX from Pharmacia Fine Chemicals (Piscataway, N.J.); agarose, polystyrene or latex beads about 1 micron to about 5 mm in diameter, polyvinyl chloride, polystyrene, cross-linked polyacrylamide, nitrocellulose or nylon-based webs such as sheets, strips, paddles, plates microtiter plate wells and the like.

It is also possible to add "linking" nucleotides to the 5' or 3' end of the member oligonucleotide, and use the linking oligonucleotide to operatively link the member to the solid support.

In nucleotide hybridizing assays, the hybridization reaction mixture is maintained in the contemplated method under hybridizing conditions for a time period sufficient for the oligonucleotides having complementarity to the predetermined sequence on the template to hybridize to complementary nucleic acid sequences present in the template to form a hybridization product, i.e., a complex containing oligonucleotide and target nucleic acid.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the target sequence, to form a nucleic acid duplex. Such time, temperature and pH conditions required to accomplish hybridization depend, as is well known in the art, on the length of the oligonucleotide to be hybridized, the degree of complementarity between the oligonucleotide and the target, the guanidine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 4 degrees C. (4° C.) to 37° C., preferably about 12° C. to about 30° C., more preferably about 22° C., and for time periods from 0.5 seconds to 24 hours, preferably 2 minutes (min) to 1 hour. Exemplary are the conditions described in Example 1.

Hybridization can be carried out in a homogeneous or heterogeneous format as is well known. The homogeneous hybridization reaction occurs entirely in solution, in which both the oligonucleotide and the nucleic acid sequences to be hybridized (target) are present in soluble forms in solution. A heterogeneous reaction involves the use of a matrix that is insoluble in the reaction medium to which either the oligonucleotide, polynucleotide probe or target nucleic acid is bound.

Where the nucleic acid containing a target sequence is in a double-stranded (ds) form, it is preferred to first denature the dsDNA, as by heating or alkali treatment, prior to conducting the hybridization reaction. The denaturation of the dsDNA can be carried out prior to admixture with a oligonucleotide to be hybridized, or can be carried out after the admixture of the dsDNA with the oligonucleotide.

Predetermined complementarity between the oligonucleotide and the template is achieved in two alternative manners. A sequence in the template DNA may be known, such as where the primer to be formed can hybridize to known glucocerebrosidase sequences and initiates primer extension into a region of DNA for sequencing purposes, as well as subsequent assaying purposes as described herein, or where previous sequencing has determined a region of nucleotide sequence and the primer is designed to extend from the recently sequenced region into a region of unknown sequence. This latter process has been referred to a "directed sequencing" because each round of sequencing is directed by a primer designed based on the previously determined sequence.

Effective amounts of the oligonucleotide present in the hybridization reaction admixture are generally well known and are typically expressed in terms of molar ratios between the oligonucleotide to be hybridized and the template. Preferred ratios are hybridization reaction mixtures containing equimolar amounts of the target sequence and the oligonucleotide. As is well known, deviations from equal molarity will produce hybridization reaction products, although at lower efficiency. Thus, although ratios where one component can be in as much as 100 fold molar excess relative to the other component, excesses of less than 50 fold, preferably less than 10 fold, and more preferably less the 2 fold are desirable in practicing the invention.

(a) Detection of Membrane-Immobilized Target Sequences

In the DNA (Southern) blot technique, DNA is prepared by PCR amplification as previously discussed. The PCR products (DNA fragments) are separated according to size in an agarose gel and transferred (blotted) onto a nitrocellulose or nylon membrane. Conventional electrophoresis separates fragments ranging from 100 to 30,000 base pairs while pulsed field gel electrophoresis resolves fragments up to 20 million base pairs in length. The location on the membrane a containing particular PCR product is determined by hybridization with a specific, labeled nucleic acid probe.

In preferred embodiments, PCR products are directly immobilized onto a solid-matrix (nitrocellulose membrane) using a dot-blot (slot-blot) apparatus, and analyzed by probe-hybridization. See U.S. Pat. Nos. 4,582,789 and 4,617,261.

Immobilized DNA sequences may be analyzed by probing with allele-specific oligonucleotide (ASO) probes, which are synthetic DNA oligomers of approximately 20 nucleotides, preferably 17 nucleotides in length. These probes are long enough to represent unique sequences in the genome, but sufficiently short to be destabilized by an internal mismatch in their hybridization to a target molecule. Thus, any sequences differing at single nucleotides may be distinguished by the different denaturation behaviors of hybrids between the ASO probe and normal or mutant targets under carefully controlled hybridization conditions.

(b) Detection of Target Sequences in Solution

Several rapid techniques that do not require nucleic acid purification or immobilization have been developed. For example, probe/target hybrids may be selectively isolated on a solid matrix, such as hydroxylapatite, which preferentially binds double-stranded nucleic acids. Alternatively, probe nucleic acids may be immobilized on a solid support and used to capture target sequences from solution. Detection of the target sequences can be accomplished with the aid of a second, labeled probe that is either displaced from the support by the target sequence in a competition-type assay or joined to the support via the bridging action of the target sequence in a sandwich-type format.

In the oligonucleotide ligation assay (OLA), the enzyme DNA ligase is used to covalently join two synthetic oligonucleotide sequences selected so that they can base pair with a target sequence in exact head-to-tail juxtaposition. Ligation of the two oligomers is prevented by the presence of mismatched nucleotides at the junction region. This procedure allows for the distinction between known sequence variants in samples of cells without the need for DNA purification. The joint of the two oligonucleotides may be monitored by immobilizing one of the two oligonucleotides and observing whether the second, labeled oligonucleotide is also captured.

(c) Scanning Techniques for Detection of Base Substitutions

Three techniques permit the analysis of probe/target duplexes several hundred base pairs in length for unknown single-nucleotide substitutions or other sequence differences. In the ribonuclease (RNase) A technique, the enzyme cleaves a labeled RNA probe at positions where it is mismatched to a target RNA or DNA sequence. The fragments may be separated according to size and the approximate position of the mutation identified. See U.S. Pat. No. 4,946,773.

In the denaturing gradient gel technique, a probe-target DNA duplex is analyzed by electrophoresis in a denaturing gradient of increasing strength. Denaturation is accompanied by a decrease in migration rate. A duplex with a mismatched base pair denatures more rapidly than a perfectly matched duplex.

A third method relies on chemical cleavage of mismatched base pairs A mismatch between T and C, G, or T, as well as mismatches between C and T, A, or C, can be detected in heteroduplexes. Reaction with osmium tetroxide (T and C mismatches) or hydroxylamine (C mismatches) followed by treatment with piperidine cleaves the probe at the appropriate mismatch.

(4) Preferred Embodiments

In view of the foregoing, the present invention contemplates a screening method comprising treating, under amplification conditions, a sample of genomic DNA isolated from a human with a PCR primer pair for amplifying a region of human genomic DNA containing nucleotide (nt) positions 57 and 58 of glucocerebrosidase exon 2. (Amplification conditions include, in an amount effective for polypeptide synthesis, the presence of PCR buffer and a thermocycling temperature.) The PCR product thus produced is then assayed for the presence of a guanine nucleotide insertion mutation adjacent to nt 57 of the exon 2. Preferably, the PCR product contains a continuous nucleotide sequence written from 5' to 3' direction represented by the formula:

5'-GAATGTCCCAAGCCTTTGAGTAGG-
GTAAGCATCATGGCTGGCAG
CCTCACAGGATTNCTTCTACTTCAGG-
CAGTG-3' (SEQ ID NO 2)

wherein N is either G, as in a normal glucocerebrosidase gene, or GG, as in a mutant gene, or a fragment thereof containing nt 57 and nt 58 of exon 2.

Preferably, the PCR primer pair comprises a first primer that hybridizes to an anti-sense strand of the exon 2 at a location 5' to nucleotide 57 of the exon, and a second primer that hybridizes to a sense strand of the exon 2 at a location 3' to nucleotide 56 of the exon. A preferred first primer is represented by the formula, 5'-GAATGTCCCAAGCCTTTGA-3' (SEQ ID NO 3), and a preferred second primer is represented by the formula, 5'-CACTGCCTGAAGTAGATGC-3' (SEQ ID NO 4).

In one preferred embodiment, the PCR product is assayed for the nt 57G mutation by treating the amplification product, under hybridization conditions, with an oligonucleotide probe specific for the nt 57G mutation, and detecting the formation of any hybridization product. A preferred oligonucleotide probe contains a nucleotide sequence represented by the formula, 5'-ACAG-GATTGGCTTCTACT-3' (SEQ ID NO 5).

In another preferred embodiment, PCR primer pair produces an amplification product containing a preselected restriction enzyme site if the mutation is present. Assaying comprises treating, under restriction conditions, the amplification product with a restriction enzyme that recognizes the preselected site, and detecting the presence of restriction products. Preferably, the restriction endonuclease is Bsa BI and the preselected restriction site is represented by the formula:

5'-GATTGGCATC-3' (SEQ ID NO 6)

Also contemplated is a screening method wherein a PCR admixture is formed by combining, in a PCR buffer, a sample of genomic DNA and a glucocerebrosidase gene-specific PCR primer pair defined by 3' and 5' primers. The 3' primer is capable of priming within a region of human genomic DNA corresponding to nucleotide positions 1-20 of glucocerebrosidase gene intron 2. The 5' primer is capable of priming within a region of human genomic DNA corresponding to nucleotide positions 1-57 of glucocerebrosidase gene. The PCR admixture thus formed is subjected to a plurality of PCR thermocycles to produce a glucocerebrosidase gene amplification product. The amplification product is then treated, under hybridization conditions, with an oligonucleotide probe specific for the insertion mutation. Any hybridization products produced are then detected. Preferably, the 5' primer is represented by the formula, 5'-GAATGTCCCAAGCCTTTGA-3' (SEQ ID NO 3). Preferably, the 3' primer is represented by the formula, 5'-CACTGCCTTGACTCACTCAC-3' (SEQ ID NO 7). Oligonucleotide hybridization to target nucleic acid is described in U.S. Pat. No. 4,530,901.

In preferred embodiments, PCR amplification products are assayed with both a probe or probes specific for a mutation and a corresponding probe or probes specific for the normal gene sequence.

C. Primers and Probes

The present invention further contemplates polynucleotide synthesis primers have nucleotide sequences represented by SEQ ID NO 3, SEQ ID NO 4, SEQ ID NO 7, SEQ ID NO 17, and SEQ ID NO 18.

Also contemplated are oligonucleotide probes having nucleotide sequences represented by SEQ ID NO 5, SEQ ID NO 8, SEQ ID NO 9, SEQ ID NO 10, SEQ ID NO 11, and SEQ ID NO 12.

EXAMPLES

The following examples are intended to illustrate but are not to be construed as limiting of the specification and claims in any way.

1. Detection of Insertion Mutations in Genomic DNA From Gaucher Disease Patients

A. Preparation and Sequencing of Genomic DNA

High molecular weight DNA was extracted from the white blood cells from a Gaucher disease patient with the 1226G/? Pv1.1−/Pv1.1+ genotype. The diagnosis of Gaucher disease was well-established in all patients, either by histopathologic study of the marrow or demonstration of diagnostically lowered levels of acid beta-glucosidase in peripheral blood cells. Classification by ethnic origin was according to the family history provided by each patient. Four half-Jewish patients were excluded from the analysis. Otherwise, all Gaucher disease patients from which DNA was available were included in the assays described below.

In the genotype described above, one allele has a point mutation of a guanine nucleotide for an adenine nucleotide at the 1226 nucleotide position of the glucocerebrosidase cDNA. This mutation will hereinafter be referred to by its exon location at nucleotide position 2 in exon 9 of the glucocerebrosidase gene. Unidentified Gaucher disease alleles are designated as "?". The glucocerebrosidase genotype is also sometimes characterized by a restriction polymorphism with the restriction endonuclease, Pvu II, which exists in intron 6 of the glucocerebrosidase gene. Alleles containing this polymorphism are designated as Pvu1.1+.

Blood was collected after informed consent from medication-free normal volunteers and anticoagulated with a mixture of 0.14M citric acid, 0.2M trisodium citrate, and 0.22M dextrose. The anticoagulated blood was centrifuged at 800×g for 15 minutes at room temperature and the platelet-rich plasma supernatant was discarded. The pelleted erythrocytes, mononuclear and polynuclear cells were resuspended and diluted with a volume equal to the starting blood volume with chilled 0.14M PBS, pH 7.4. The peripheral blood white blood cells were recovered from the diluted cell suspension by centrifugation on low endotoxin Ficoll-Hypaque (Sigma Chem. Corp. St. Louis, Mo.) at 400×g for 10 minutes at 18 degrees C. (18° C.). The pelleted white blood cells were then resuspended and used for the source of high molecular weight DNA.

The high molecular weight DNA was isolated from the white blood cells using methods well known to one skill in the art and described by Maniatis et al., *Molecular Cloning: A Laboratory Manual*, 2nd ed. Cold Spring Harbor Laboratory, Sections 9.16–9.23, (1989) and U.S. Pat. No. 4,683,195.

The extracted high molecular weight DNA was then digested to completion with EcoR I restriction endonuclease. The resultant digested genomic DNA was then ligated directly into the cloning vector, Lambda Dash II, (Catalog Number 247201, Stratagene, La Jolla, Calif.), which had previously digested with EcoR I. The ligation mixture was packaged according to the manufacturer's instructions using Gigapack II Gold packaging extract (Catalog Number 200214, Stratagene) and the packaged ligated mixture was plated on the *E. coli* strain LE392. To determine the presence of glucocerebrosidase genes, replica filter lifts of the genomic library were screened with a full-length (2.23 kb) glucocerebrosidase cDNA which was nick-translated and radioactively labeled with $^{32}$P. The reactive clones were distinguished from the glucocerebrosidase pseudogene clones by the fact that the functional clones did react, but the pseudogene clones did not react, with an oligonucleotide probe corresponding to a 55 base pair region in exon 9 which is deleted from the pseudogene.

Replica filter lifts of the clones having functional glucocerebrosidase genomic DNA were then probed with oligonucleotide specific probes that allowed the detection of the normal gene as well as the A to G point mutation at nucleotide 2 in exon 9. The sequences and corresponding SEQ ID NO for the oligonucleotide probes used in this screening and others in subsequent sections of the Examples are listed below in Table 1. The probe that hybridized to the normal gene is designated Exon 9 Norm whereas the probe that hybridized to the mutated gene is designated Exon 9 Mut. The underlined nucleotide corresponds to the mutation nucleotide.

TABLE I

| DESIG-NATION | SEQ ID NO | SEQUENCE |
|---|---|---|
| Exon 2 Norm | 8 | 5'-ACAGGATTGCTTCTACT-3' |
| Exon 2 Mut | 5 | 5'-ACAGGATTG<u>G</u>CTTCTACT-3' |
| Exon 9 Norm | 9 | 5'-TACCCTAGAACCTCCTG-3' |
| Exon 9 Mut | 10 | 5'-TACCCTAGA<u>G</u>CCTCCTG-3' |
| Exon 10 Norm | 11 | 5'-GAACGACCTGGACGCAG-3' |
| Exon 10 Mut | 12 | 5'-GAACGACC<u>C</u>GGACGCAG-3' |

The oligonucleotides used in practicing this invention were synthesized on an Applied Biosystems 381A DNA Synthesizer following the manufacturer's instructions. Labeling of the probes with $^{32}$P was performed by admixing 2.5 µl of 10× concentrate of kinase buffer (10×=0.5M Tris[hydroxymethyl] aminomethane hydrochloride (Tris-HCl) at pH 7.6, 0.1M MgCl$_2$, 50 mM dithiothreitol (DTT), 1 mM spermidine-HCl, and 1 mM ethylenediaminetetraacetic acid (EDTA)), 1.1 µl 60 micrograms (µg)/microliter (µl) of a selected oligonucleotide, 18.4 µl water, 2 µl of 6000 Ci/mM of gamma $^{32}$P ATP at a concentration of 150 mCi/µl, and 1 µl of 10 U/µl polynucleotide kinase. The labeling admixture was maintained for 20 minutes at 37° C. followed by 2 minutes at 68° C. The maintained admixture was then applied to a Sephadex G50 (Pharmacia, Inc., Piscataway, N.J.) spin column to remove unincorporated $^{32}$P-labeled ATP.

Glucocerebrosidase functional clones having as well as lacking, the exon 9 point mutation were selected and digested with Xba I and subcloned into a Bluescript cloning vector previously digested with Xba I. Double stranded sequencing of the resultant subclones containing glucocerebrosidase genomic DNA was performed by the chain termination technique described by Sanger et al., *Proc. Natl. Acad. Sci., U.S.A.*, 74:5463–5467 (1977) with appropriate primers based on the known glucocerebrosidase genomic sequence as described by Horowitz et al., *Genomics*, 4:87–96 (1989).

The results of sequencing the genomic DNA prepared above revealed that the allele containing the ion of an A to a G at nucleotide position 2 (cDNA nucleotide position 1226) was identical to the normal allele with the only exception that the normal allele contained a unique mutation of an insertion of a G nucleotide in exon 2 adjacent to nucleotide position 57 (cDNA nucleotide position 84, also designated 8466). The following sections of Example 1 detail the preferred approaches which were used to confirm the presence of the novel glucocerebrosidase gene mutation in Gaucher disease patients and to set forth the best mode of practicing this invention.

B. Preparation and Sequencing of cDNA

Total cellular RNA was purified from cultured lymphoblasts or fibroblasts from two unrelated patients having the 1226G/? Pv1.1−/Pv1.1+ genotype. The purification procedure was performed as described by Chomczynski et al., *Anal. Biochem.*, 162:156–159 (1987). Briefly, the cells were prepared as described in Example 1A. The cells were homogenized in 10 milliliters (ml) of a denaturing solution containing 4.0M guanidine thiocyanate, 0.1M Tris-HCl at pH 7.5, and 0.1M beta-mercaptoethanol to form a cell lysate. Sodium lauryl sarcosinate was then admixed to a final concentration of 0.5% to the cell lysate after which the admixture was centrifuged at 5000×g for 10 minutes at room temperature. The resultant supernatant containing the total RNA was layered onto a cushion of 5.7M cesium chloride and 0.01M EDTA at pH 7.5 and was pelleted by centrifugation. The resultant RNA pellet was dissolved in a solution of 10 mM Tris-HCl at pH 7.6 and 1 mM EDTA (TE) containing 0.1% sodium docecyl sulfate (SDS). After phenol-chloroform extraction and ethanol precipitation, the purified total cellular RNA concentration was estimated by measuring the optical density at 260 nm.

Poly-A+ RNA was isolated from the purified total cellular RNA using methods described by Maniatis et al., supra, Sections 7.26–7.29. Briefly, 500 milligrams (mg) of the total RNA was resuspended in one ml of 1× sample buffer (1 mM Tris-HCl at pH 7.5, 0.1 mM EDTA and 0.5M NaCl) and maintained for five minutes at 65° C. and then on ice for five more minutes. The mixture was then applied to an oligo-dT column that was previously prepared by washing the oligo-dT with a solution containing 10 mM Tris-HCl at pH 7.5, 1 mM EDTA and 0.5M NaCl. The eluate was collected in a sterile polyproplene tube and reapplied to the same column after heating the eluate for five minutes at 65° C. The oligo dT column was washed with 0.4 ml of high salt loading buffer consisting of 10 mM Tris-HCl at pH 7.5, 500 mM NaCl and 1 mM EDTA. This was followed by a wash with 2 ml of 1× low salt buffer containing 10 mM Tris-HCl at pH 7.5, 100 mM NaCl and 1 mM EDTA. The poly-A+ RNA was then eluted from the column with 0.6 ml of buffer consisting of 10 mM Tris-HCl at pH 7.5 and 1 mM EDTA. The poly-A+ RNA was purified by extracting the eluate with phenol/chloroform followed by a single extraction with 100% chloroform. The poly-A+ RNA was concentrated by ethanol precipitation and resuspended in RNase-free water.

In preparation for PCR amplification, poly-A+ RNA prepared according to the above examples was used as a template for cDNA synthesis. In a typical 50 µl transcription reaction, 50–200 nanograms (ng) of poly-A+ RNA prepared above in water was first annealed with 250 ng of the 3' sense oligonucleotide primer having the nucleotide sequence 5'-TAAGCT-CACACTGGCCCTGC-3' (SEQ ID NO 13) at 65° C. for five minutes. The definitions of sense and anti-sense primers are on page 17 of the specification. The 3' primer corresponded to nucleotide positions 198 through 217 of glucocerebrosidase exon 11. Subsequently, 12 µl of the first strand cDNA synthesis reaction admixture was admixed to a 20 µl system containing 1.0 mM each of dATP, dCTP, dGTP, and dTTP, 40 mM Tris-HCl at pH 8.0, 8 mM MgCl$_2$, 50 mM NaCl, 2 mM spermidine, 1 U of RNase block (Stratagene), and 25 U of AMV reverse transcriptase. The solution was maintained for 1 hour at 42° C. and then five minutes at 65° C. to form first strand cDNA.

Twenty µl of the first strand cDNA was then diluted with 80 µl of a PCR reaction admixture containing 250 ng of the 5' anti-sense oligonucleotide having the sequence 5'-CTCTGGAACCCCTGTGGTCT-3' (SEQ ID NO 14), and a final concentration of 1.0 mM each of dATP, dCTP, dGTP, and dTTP, 40 mM Tris-HCl at pH 8.0, 8 mM MgCl$_2$, 50 mM NaCl, 2 mM spermidine, 5% DMSO and 3.5 U of Taq polymerase. The 5' primer corresponded to the nucleotide positions 184 through 203 of glucocerebrosidase exon 1. The reaction mixture was overlaid with mineral oil and subjected to 35 cycles of amplification on a DNA Thermal Cycler (Perkin Elmer-Cetus, South Plainfield, N.J.). Each amplification cycle included denaturation at 92° C. for 30 seconds, annealing at 58° C. for 30 minutes and elongation at 72° C. for 30 seconds. The amplified cDNA samples were then extracted twice with phenol/chloroform, once with chloroform, ethanol precipitated and are stored at −70° C. in water. The amplified cDNA was comprised of a portion of the leader sequence of the cDNA which corresponded to the 5' portion of exon 1 and extended through most of entire cDNA which corresponded to exon 11 of the genomic sequence. The length of the amplified cDNA product was approximately 1768 base pairs.

For sequencing of the resultant amplified cDNA, single stranded DNA was first generated. Five to ten percent of the amplified cDNA products prepared above served as the template in a unbalanced PCR amplification where either a 5' anti-sense oligonucleotide primer having the sequence 5'-CTCTTCATC-TAATGACCCTG-3' (SEQ ID NO 15) or a 3' sense oligonucleotide primer having the sequence 5'-CCAGTGCCTCCTTGAGTA-3' (SEQ ID NO 16) was used. The 5' primer corresponded to nucleotide positions 205 through 224 of glucocerebrosidase gene exon 1. The 3' primer corresponded to nucleotide positions 116 through 133 of glucocerebrosidase gene exon 11. The PCR amplification was performed as described above with the exception of the different primers. Sequencing of the single stranded PCR-generated cDNA was accomplished with cDNA primers spaced approximately 200 nucleotides apart along the single stranded cDNA.

The sequences determined directly from the PCR-amplified cDNAs from the two patients with Gaucher disease having the 1226G/? Pv1.1−/Pv1.1+ genotype showed two abnormalities. Firstly, two bands were found in the sequencing gels at nucleotide position 1226 of the cDNA where both the normal A nucleotide and the abnormal G nucleotide were found. Thus, a heterozygous state for the 1226G mutation was confirmed. Secondly, an insertion of a G nucleotide was present adjacent to nucleotide position 84 of the cDNA (84GG). Two bands were apparent at each position in the sequencing gel after the inserted G nucleotide representing the sequences of the displaced mutant and the 1226G mutant which did not have the 84GG insertion. Thus, the sequencing of the cDNA confirmed the presence of a unique insertion mutation of a G nucleotide in patients having Gaucher disease adjacent to nucleotide position 84 of the glucocerebrosidase cDNA which corresponds to the nucleotide position adjacent to nucleotide 57 of exon 2. In addition, since the relative amounts of the two alleles of the patient heterozygous for the 1226G mutation were equivalent, the Gaucher disease, thus, was not the result of a defect in transcription.

C. Preparation and Detection of Translated Glucocerebrosidase Protein by In Vitro Translation of cDNA To determine whether the Gaucher disease resulting from the insertion mutation in exon 2 of the glucocerebrosidase gene was the result of a non-functional protein or whether it was the result from a lack of translation of the mRNA altogether, in vitro translation assays were performed. For these assays, the amplified cDNA produced in Example 1B was cloned into a Bluescript SK vector (Stratagene) following a second PCR amplification to generate the restriction endonuclease sites, EcoR I and Xba I. A 5' anti-sense oligonucleotide primer was used to amplify the EcoR I site and a 3' sense oligonucleotide primer was used to amplify the Xba I site. The resultant construct was then used to prepare RNA for the in vitro translation assays.

The cDNA clones cloned into Bluescript SK were first analyzed to determine if the 1226G point mutation or the 84GG insertion mutation was present. The clones were first linearized with Xba I. One μg of each linearized clone was then admixed to the transcriptions system described by Sorge et al., Am. J. Hum. Genet., 41:1016–1024 (1987). Briefly, the linearized DNA was then treated with Proteinase K (Promega Biotec, Madison, WI) and then the treated DNA was admixed to a solution containing 0.8 mM each of ATP, GTP, CTP and UTP, 30 mM DTT, 40 mM Tris-HCl at pH 8.0, 8 mM $MgCl_2$, 2 mM spermidine, 50 mM NaCl, 25 U RNase block and 10–30 U of T7 DNA polymerase. The admixture was maintained for 30 minutes at 37° C. to form transcribed RNA. After phenol and chloroform extraction and ethanol precipitation, the RNA transcripts were redissolved in 25 μl water. Three μl of the dissolved RNA was then directly admixed to 20 μl of rabbit reticulolysate (Amersham, Arlington Heights, Ill.) and 2 μl (400 μCi) of $^{35}S$-methionine After a 30 minute maintenance at 30° C., the translated proteins were electrophoresed on a 10% Laemmli SDS-PAGE gel.

The results of the in vitro translation assays showed that little or no glucocerebrosidase protein attributed to the allele of the Pv1.1+ haplotype lacking the 1226G mutation, was produced. Thus, despite the normal amount of mRNA transcribed, no protein was translated. The insertion mutation of a G nucleotide adjacent to nucleotide position 84 in the cDNA was in the portion of the gene that was translated to the leader sequence. The insertion mutation resulted in a frame shift that caused a stop codon to appear 18 amino acid residues downstream from the insertion. Accordingly, patients expressing the allele having the insertion mutation do not have any glucocerebrosidase protein produced from that allele. The clinical disorder produced in patients heterozygous for the 1226G mutation linked with the Pv1.1− haplotype and the 84GG mutation linked with the Pv1.1+ haplotype is more severe than that observed for 1226G homozygotes.

D. Preparation and Detection of Designed Restriction Sites for Identifying the Insertion Mutation The presence of an insertion mutation of a G nucleotide in the glucocerebrosidase gene exon 2 adjacent to nucleotide position 57 (cDNA nucleotide position 84) was confirmed using mismatch PCR as described by Kumar et al., Oncogene Res., 1:235–241 (1989). In mismatch PCR, one of the two oligonucleotide primers used for PCR amplification of genomic DNA is designed to contain one or more mismatches that create a restriction endonuclease site in the mutant but not in the normal allele. Thus, PCR amplification products generated with the two primers will contain the restriction endonuclease cleavage site only if they were derived from the mutated locus. Amplified segments from the normal allele only contain the introduced mismatches and thus, lack the cleavage site. Mutant and normal alleles are easily distinguished as the mutant allele will be cleaved into two fragments with the specific restriction endonuclease while the normal allele will remain intact.

The primers for amplifying the region of DNA having the insertion mutation were designed so that only the functional glucocerebrosidase gene would be amplified and not the pseudogene. The 5' anti-sense oligonucleotide primer mismatched the pseudogene at two positions, nucleotide positions 17 and 19, and has the sequence 5'-GAATGTCCCAAGCCTTTGA-3' (SEQ ID NO 3). The 5' primer corresponded to the nucleotide positions 1 through 19 of glucocerebrosidase exon 2. The 3' sense oligonucleotide primer differed from the glucocerebrosidase sequence at one position in order to create a Bsa BI restriction endonuclease site when two G nucleotides were present at nucleotide positions 57 and 58 of exon 2 compared to the normal sequence of a G nucleotide followed by C. The sequence of the 3' primer is 5'-CACTGCCTGAAGTAGATGC-3' (SEQ ID NO 4). The T nucleotide in the 17th position was the mismatched nucleotide. The 3' primer corresponded to the exon 2 nucleotide positions from 57 through 75 of the glucocerebrosidase gene.

PCR amplification to determine the presence or absence of the insertion mutation was performed on 0.5 μg of genomic DNA prepared in Example 1A in a 1× PCR buffer (20× PCR buffer was prepared by admixing 670 μl Tris-HCl at pH 8.8, 166 μl 2M ammonium sulfate, 134 μl $MgCl_2$, 42.5 μl of an 80 mg/ml solution of bovine serum albumin and water up to 2 ml) containing 0.5 mM each of dATP, dGTP, dCTP and dTTP, 5% DMSO, 300 ng of each oligonucleotide primer described above and 3 U Taq DNA polymerase (Boehringer Mannheim, Indianapolis, Ind.). Twenty-eight amplification cycles of PCR were performed as described in Example 1B to form amplified glucocerebrosidase exon 2 products, where each cycle consisted of denaturation for 30 seconds at 92° C., annealing for 30 seconds at 59° C. and extending for 30 seconds at 72° C.

Fifteen μl of the amplified glucocerebrosidase exon 2 products were then maintained in a 50 μl digestion system with 1× New England Biolabs Buffer Number 2 (New England Biolabs, Beverly, Mass.) and 20 U Bsa BI restriction endonuclease for 1.5 hours at 60° C. After admixture of 2.5 volumes of ethanol followed by chilling, the precipitate was dried, redissolved in 15 μl gel loading dye buffer and electrophoresed on a 12% acrylamide gel.

PCR amplified genomic DNA having the insertion mutation of a G nucleotide in glucocerebrosidase exon 2 adjacent to nucleotide 57 (cDNA nucleotide position 84) was cleaved into two fragments of 57 and 18 base pairs each. The normal allele was not cleaved as verified by visualizing only one fragment of 75 base pairs. Thus, mismatch PCR to generate a Bsa BI restriction site in genomic DNA from heterozygous patients having the genotype described in Example 1A confirmed the presence of an insertion mutation in glucocerebrosidase exon 2 adjacent to nucleotide position 57. Other restriction endonuclease cleavage sites can be designed to function in mismatch PCR to identify the insertion mutation. The type of primer used for producing a Bsa BI site is preferred, however, in that the oligonucleotide primers do not amplify the pseudogene and amplification can be performed in one reaction.

E. Preparation of PCR Amplified Genomic DNA Containing the Insertion Mutation and Detection by Allele Specific Oliognucleotide Hybridization The insertion mutation of a G nucleotide in glucocerebrosidase exon 2 was determined by another approach in which PCR amplified genomic DNA containing the mutation was detected by hybridization with oligonucleotide probes that hybridize to that region. To amplify the exon 2 region having the insertion mutation which will be hybridized to oligonucleotide specific probes, PCR amplifications were performed as essentially described in Example 1D with the following exceptions: The 3' sense oligonucleotide primer corresponded to the nucleotide positions 1 through 20 of intron 2 of the glucocerebrosidase gene. The primer hybridized to the first 20 nucleotides in intron 2 which is located 3' to exon 2 and, thus, 3' to the location of the insertion mutation. The 3' primer has the sequence 5'-CACTGCCTTGACTCACTCAC-3' (SEQ ID NO 7). The C nucleotide in position 20 was a mismatch with the pseudogene therefore, the primer did not hybridize to it. The pseudogene, thus, was not amplified relative to the functional gene; and 2) Both the 5' anti-sense oligonucleotide primer which was the oligonucleotide primer described above were used at 250 ng/μl.

Following the PCR amplification, 2 μl of the amplified glucocerebrosidase exon 2 DNA products were spotted onto separate sheets of nitrocellulose. After the spotted amplified DNA had dried, the nitrocellulose was treated with 0.5N NaOH for 2 minutes, 1M Tris-HCl at pH 7.5 for 2 minutes, and then 0.5M Tris-HCl at pH 7.5 containing 1.5M NaCl for 2 minutes to denature and then neutralize the DNA. The resultant filters were baked under a vacuum for 1 hour at 80° C., were prehybridized for at least 20 minutes at 42° C. with a prehybridization solution consisting of 6× SSC (1× =0.15M NaCl, 0.15M sodium citrate), 5× Denhardt's solution (5× =0.1% polyvinylpyrrolidone, 0.1% ficoll, and 0.1% bovine serum albumin), 5 mM sodium phosphate buffer at pH 7.0, 0.5 mg/ml salmon testis DNA and 1% SDS.

After the prehybridization step, the nitrocellulose filters were exposed to $^{32}$P-labeled oligonucleotide probes diluted in prehybridization buffer. The oligonucleotide probes used in to hybridize to exon 2 amplification products are shown in Table 1 in Example 1A. The probes were labeled as described in Example 1A and $10 \times 10^6$ cpm of each labeled probe was separately admixed with each filter. The nitrocellulose filters were then maintained overnight at 42° C. to allow for the formation of hybridization products. The nitrocellulose filters exposed to the exon 2 normal probe were washed with 6× SSC containing 0.1% SDS at 46° C. whereas the filters exposed to the exon 2 mutant probe were washed with the same solution at a more stringent temperature of 52° C. The nitrocellulose filters were then dried and subjected to radioautography.

The results of the allele specific oligonucleotide hybridization showed that amplified genomic DNA exon 2 products that are normal in the region of the probe hybridized to the exon 2 normal probe. Only those exon 2 products having the insertion mutation adjacent to nucleotide 57 in exon 2 hybridized with the mutant probe. Positive and negative controls were included in each assay to determine whether the PCR amplification was successful. The patients' genomic DNA prepared in Example 1A were determined by this alternative approach to have the unique insertion mutation of a G nucleotide in glucocerebrosidase exon 2 adjacent to nucleotide position 57 (cDNA nucleotide position 84).

2. Simultaneous Detection of an Insertion Mutation and Two Point Mutations in Genomic DNA from Gaucher Disease Patients

A. Preparation of PCR Amplified Genomic DNA

In addition to the insertion mutation in glucocerebrosidase exon 2, other single-base substitutions have been reported to cause Gaucher disease. See, Beutler et al., *Clin. Chim. Acta*, 194:161–166 (1990); Zimran et al., *Lancet*, ii:349–352 (1989); Tsuji et al., *N. Engl. J. Med.*, 316:570–621 (1987); Tsuji et al., *Proc. Natl. Acad. Sci., U.S.A.*, 85:2349–2352 (1988); Reiner et al., *DNA*, 7:107–116 (1988); Grabowski et al., *CRC Crit. Rev. Biochem. Mol. Biol.*, 25:385–414 (1990); and Graves et al., *DNA* 7:521–528 (1988). The most common base substitution, also called a point mutation, occurs in exon 9 of the glucocerebrosidase gene at nucleotide position 2 which corresponds to cDNA nucleotide position 1226. At this position, an adenine nucleotide has been substituted by a guanine nucleotide. Another point mutation occurs in exon 10 of the glucocerebrosidase gene at nucleotide position 60 which corresponds to cDNA nucleotide position 1448. At this position, a thymine nucleotide has been substituted by a cytosine nucleotide.

The glucocerebrosidase pseudogene that is highly homologous with the functional glucocerebrosidase gene complicates detection of mutations that cause Gaucher disease. In order to detect mutations that were present on the functional gene, methods were developed to amplify regions of the functional gene without contamination from the pseudogene (Beutler et al., supra). Recently, cDNAs that were cloned and sequenced from mRNA isolated from cultured skin fibroblasts of Gaucher disease patients revealed the presence of a fusion gene having a 5' end comprised of the functional gene and the 3' end comprised of the pseudogene (Zimran et al., *J. Clin. Invest.*, 85:219–222 (1990)). Thus, a cross-over between functional and non-functional pseudogenes has occurred.

As the point mutation (T→C) in exon 10 at nucleotide position 60 (cDNA 1448) is present in the pseudogene, it is advantageous, when screening for mutations in the population, to screen all genes including those fusion genes which contain certain mutations such as the one in exon 10. If a cross-over event occurs 5' or upstream of exon 10, the nucleotide position of the mutation in exon 10 will remain the same. However, if an unequal cross-over event occurs sufficiently 5' to the mutation, the nucleotide position of the mutation in exon 10 may change.

Based on the foregoing discussion, a preferred embodiment of this invention is the capacity to screen the glucocerebrosidase gene, the pseudogene and any fusion genes to obtain a improved analysis of the presence of mutations for correlation with the severity of the disease. The method for accomplishing the detection of the exon 2, exon 9 and exon 10 mutations in both normal functional genes and fusion genes where a cross-over has occurred is presented below.

Genomic DNA was isolated from patients with Gaucher disease as described in Example 1A. Two separate genomic DNA fragments of the glucocerebrosidase gene were then amplified with specific oligonucleotide primers shown in Table 2 below with the corresponding SEQ ID NOs.

TABLE 2

| DESIGNATION | SEQ ID NO | SEQUENCE |
|---|---|---|
| Exon 2 | 3 | 5'-GAATGTCCCAAGCCTTTGA-3' |
| Intron 2 | 7 | 5'-CACTGCCTTGACTCACTCAC-3' |
| Intron 7 | 17 | 5'-CAAGGTCCAGGATCAGTTGC-3' |
| Intron 10 | 18 | 5'-AACGCTGTCTTCAGCCCACT-3' |

The first genomic DNA fragment was amplified with the oligonucleotide primers designated exon 2 (a 5' anti-sense primer) and intron 2 (a 3' sense primer) as listed in Table 2. These primers when used in PCR amplification as described below resulted in the generation of a 107 base pair fragment in which the exon 2 insertion mutation (cDNA 84GG) could be identified, if present. The intron 2 oligonucleotide primer mismatches the pseudogene at two nucleotide positions, therefore, only the functional glucocerebrosidase gene was amplified.

The second genomic DNA fragment was amplified with the oligonucleotide primers designated intron 7 (a 5' anti-sense primer) and intron 10 (a 3' sense primer) as listed in Table 2. These primers when used in PCR amplification as described below resulted in the generation of a 1352 base pair fragment in which both the exon 9 and 10 point mutations (cDNA 1226 and 1448, respectively) could be identified if present in the functional gene as well as in fusion cross-over genes. The intron 7 oligonucleotide primer mismatched the pseudogene at five nucleotide positions, therefore, only the functional gene was amplified. The intron 10 oligonucleotide primer, in contrast, matched both the functional gene and the pseudogene. Therefore, when intron 10 primer was used in conjunction with the intron 7 primer, both functional genes and genes having cross-overs occurring between the regions of the two primers of the functional gene and the pseudogene, were amplified.

The PCR conditions used in the amplifying the resultant PCR products described above were performed as described in Example 1D with the exceptions that 150 ng of each oligonucleotide primer and 0.75 U of Taq DNA polymerase were used. Twenty-eight PCR cycles were performed as described in Example 1D. The resultant PCR products were then blotted onto nitrocellulose filters as described in Example 1E for subsequent hybridization with labeled allele specific oligonucleotide probes as described below.

B. Detection of Mutations by Allele Specific Oliognucleotide Hybridization

The PCR products immobilized on nitrocellulose filters prepared in Example 2B above were treated under hybridization conditions as described in Example 1E. The oligonucleotide probes used to detect the mutations in exon 2, exon 9 and exon 10 are shown in Table 1 in Example 1A. Both the normal and mutant probes were used to identify alleles having normal and mutant genotypes. The normal probes hybridized only to alleles that were normal in the region of the probe and whereas the mutant probes hybridized to only those alleles having the specific mutation. The results of the PCR amplification performed as described above on genomic DNA from Gaucher disease patients revealed that all three mutations could be amplified simultaneously from one PCR reaction and subsequently detected with allele specific oligonucleotide probes. Mutations present in the functional glucocerebrosidase gene as well as in fusion genes in which cross-overs between functional and pseudogene occurred between the two oligonucleotide primer pairs (intron 7 and intron 10) were readily detected using this protocol. Thus, the correlation of the presence of the mutations with the severity of the disease is more readily achieved with this preferred one step PCR amplification.

In summary, over 95% of the disease producing alleles have been identified at the DNA level in 71 Jewish subjects with Gaucher disease. Most of these were mutations at cDNA nucleotide positions 84, 1226, and 1448, (corresponding to exon 2, exon 9 and exon 10 mutations, respectively) and screening for these three mutations accounts for 94.4% of the Gaucher producing alleles in this group of patients. Among the non-Jewish patients the 1226G and 84GG mutations Were less common. While these genes apparently achieve polymorphic frequencies in the Jewish population they are much less common in non-Jews. As a consequence more sporadic mutations are present in the non-Jewish population and only 75% of the disease producing alleles were identified. The invention described herein provides a means for the detection of the novel insertion mutation in exon 2 in addition to the point mutations in exon 9 and 10 in the glucocerebrosidase gene complex.

The foregoing specification, including the specific embodiments and examples, is intended to be illustrative of the present invention and is not to be taken as limiting. Numerous other variations and modifications can be effected without departing from the true spirit and scope of the invention.

What is claimed is:

1. A human genetic screening method for identifying a glucocerebrosidase gene mutation comprising detecting in a nucleic acid sample isolated from a human an insertion of a guanine nucleotide adjacent to nucleotide position 57 of glucocerebrosidase gene exon 2, thereby identifying said mutation.

2. The method according to claim 1 further comprising additionally detecting in said nucleic acid sample the presence of a glucocerebrosidase gene point mutation characterized as a change from an adenine nucleotide to a guanine nucleotide at nucleotide position 2 of glucocerebrosidase gene exon 9.

3. The method according to claim 1 further comprising additionally detecting in said nucleic acid sample the presence of a glucocerebrosidase gene point mutation characterized as a change from a thymine nucleotide to a cytosine nucleotide at nucleotide position 60 of glucocerebrosidase gene exon 10.

4. A human genetic screening method for identifying a glucocerebrosidase gene insertion mutation comprising:

(a) treating, under amplification conditions, a sample of genomic DNA from a human with a polymerase chain reaction (PCR) primer pair for amplifying a region of human genomic DNA containing nucleotide positions 57 and 58 of glucocerebrosidase gene exon 2, said treating producing an amplification product containing said region; and (b) detecting in the amplification product of step (a) for presence of a guanine (G) nucleotide insertion mutation after nucleotide position 57 of said exon, thereby identifying said mutation.

5. The method according to claim 4 wherein said region contains a nucleotide sequence represented by SEQ ID NO 19, or a fragment thereof.

6. The method according to claim 5 wherein said region consists essentially of a nucleotide sequence represented by SEQ ID NO 2.

7. The method according to claim 4 wherein said detecting comprises treating, under hybridization conditions, the amplification product of step (a) with an oligonucleotide probe specific for said insertion mutation, and detecting the formation of a hybridization product.

8. The method according to claim 7 wherein said oligonucleotide probe contains a nucleotide sequence represented by the formula, 5'-ACAGGATTGGCT-CTACT-3' (SEQ ID NO 5).

9. The method according to claim 4 wherein said PCR primer pair produces an amplification product containing a preselected restriction enzyme site if said mutation is present, and said detecting of step (b) comprises treating, under restriction conditions, the amplification product of step (a) with a restriction enzyme that recognizes said site, and detecting the presence of restriction products.

10. The method according to claim 4 wherein said PCR primer pair comprises:
  (i) a first primer that hybridizes to an anti-sense strand of said exon 2 at a location 5' to nucleotide 57 of said exon; and
  (ii) a second primer that hybridizes to a sense strand of said exon 2 at a location 3' to nucleotide 56 of said exon.

11. The method according to claim 10 wherein said first primer of step (i) is represented by the formula, 5'-GAATGTCCCAAGCCTTTGA-3' (SEQ ID NO 3).

12. The method according to claim 10 wherein said second primer of step (ii) is represented by the formula, 5'-CACTGCCTGAAGTAGATGC-3' (SEQ ID NO 4).

13. The method according to claim 10 wherein said second primer encodes a preselected restriction endonuclease site, and step (b) comprises treating the amplification product of step (a) with a restriction endonuclease that recognizes said preselected restriction site.

14. The method according to claim 11 wherein said restriction endonuclease i Bsa BI and said preselected restriction site is represented by the formula:

5'-GATTGGCATC-3' (SEQ ID NO 6).

15. A method for detecting in a human a Gaucher disease allele containing an insertion mutation comprising insertion of a guanine (G) nucleotide after nucleotide position 57 of glucocerebrosidase gene exon 2, which method comprises:
  (a) forming a polymerase chain reaction (PCR) admixture by combining, in a PCR buffer, a sample of genomic DNA from said human and a glucocerebrosidase gene-specific PCR primer pair defined by 3' and 5' primers, said 3' primer priming within a region of human genomic DNA corresponding to nucleotide position 1-20 of glucocerebrosidase gene intron 2, and said 5' primer priming within a region of human genomic DNA corresponding to nucleotide positions 1-57 of said glucocerebrosidase gene;
  (b) subjecting said PCR admixture to a plurality of PCR thermocycles to produce a glucocerebrosidase gene amplification product;
  (c) treating, under hybridization conditions, said amplification product with an oligonucleotide probe specific for said insertion mutation; and
  (d) detecting hybridization products produced in step (c), thereby detecting said mutation.

16. The method according to claim 15 wherein said 5' primer of step (a) is represented by the formula, 5'-GAATGTCCCAAGCCTTTGA-3' (SEQ ID NO 3).

17. The method according to claim 15 wherein said 3' primer of step (a) is represented by the formula, 5'-CACTGCCTTGACTCACTCAC-3' (SEQ ID NO 7).

18. The method according to claim 15 wherein said probe of step (c) is represented by the formula, 5'-ACAGGATTGGCTTCTACT-3' (SEQ ID NO 5).

19. A human genetic screening method for identifying preselected glucocerebrosidase gene mutations comprising:
  (a) treating, under amplification conditions, a sample of genomic DNA from a human with a polymerase chain reaction (PCR) primer pair for amplifying a region of human genomic DNA containing nucleotide positions 57 and 58 of glucocerebrosidase gene exon 2, said treating producing a first amplification product containing said region; and
  (b) treating, under amplification conditions, a sample of genomic DNA from said human with a polymerase chain reaction (PCR) primer pair for amplifying a region of human genomic DNA containing nucleotide position 2 of glucocerebrosidase gene exon 9 and nucleotide position 60 of glucocerebrosidase exon 10, said treating producing a second amplification product containing said region;
  (c) detecting in said first amplification product of step (a) the presence of a guanine nucleotide insertion mutation after nucleotide position 57 of said exon;
  (d) detecting in said second amplification product of step (b) the presence of a guanine nucleotide point mutation at nucleotide position 2 of said exon; and
  (e) detecting in said second amplification product of step (b) the presence of a cytosine nucleotide point mutation at nucleotide position 60 of said exon, thereby detecting said mutations.

20. The method according to claim 19 wherein said primer pair of step (a) comprises 5' and 3' primers, said 5' primer priming within a region of human genomic DNA corresponding to nucleotide positions 1-57 of said glucocerebrosidase gene exon 2, and said 3' primer priming within a region of human genomic DNA corresponding to nucleotide positions 1-20 of said glucocerebrosidase gene intron 2.

21. The method according to claim 20 wherein said 5' primer of step (a) is represented by the formula, 5'-GAATGTCCCAAGCCTTTGA-3' (SEQ ID NO 3).

22. The method according to claim 20 wherein said 3' primer of step (a) is represented by the formula, 5'-CACTGCCTTGACTCACTCAC-3' (SEQ ID NO 7).

23. The method according to claim 19 wherein said primer pair of step (b) comprises 5' and 3' primers, said 5' primer priming within a region of human genomic DNA corresponding to nucleotide positions 841-860 of said glucocerebrosidase gene intron 7, and said 3' primer priming within a region of human genomic DNA corresponding to nucleotide positions 26-45 of said glucocerebrosidase gene intron 10.

24. The method according to claim 23 wherein said 5' primer is represented by the formula, 5'-CAAGGTCCAGGATCAGTTGC-3' (SEQ ID NO 17).

25. The method according to claim 23 wherein said 3' primer is represented by the formula, 5'-AACGCTGTCTTCAGCCCACT-3' (SEQ ID NO 18).

26. The method according to claim 19 wherein said detecting of step (c) comprises treating, under hybridization conditions, said amplification product with an oligonucleotide probe represented by the formula, 5'-ACAGGATTGGCTTCTACT-3' (SEQ ID NO 5).

27. The method according to claim 19 wherein said detecting of step (d) comprises treating, under hybridization conditions, said amplification product with an oligonucleotide probe represented by the formula, 5'-TACCCTAGAGCCTCCTG-3' (SEQ ID NO 10).

28. The method according to claim 19 wherein said detecting of step (e) comprises treating, under hybridization conditions, said amplification product with an oligonucleotide probe represented by the formula, 5'-GAACGACCCGGACGCAG-3' (SEQ ID NO 12).

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
      ( A ) LENGTH: 7620 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: exon
    ( B ) LOCATION: 356..611
    ( D ) OTHER INFORMATION: /product="Exon 1"

( i x ) FEATURE:
    ( A ) NAME/KEY: intron
    ( B ) LOCATION: 612..979
    ( D ) OTHER INFORMATION: /function="Intron 1"

( i x ) FEATURE:
    ( A ) NAME/KEY: exon
    ( B ) LOCATION: 980..1067
    ( D ) OTHER INFORMATION: /product="Exon 2"

( i x ) FEATURE:
    ( A ) NAME/KEY: intron
    ( B ) LOCATION: 1068..1619
    ( D ) OTHER INFORMATION: /function="Intron 2"

( i x ) FEATURE:
    ( A ) NAME/KEY: exon
    ( B ) LOCATION: 1620..1811
    ( D ) OTHER INFORMATION: /product="Exon 3"

( i x ) FEATURE:
    ( A ) NAME/KEY: intron
    ( B ) LOCATION: 1812..1934
    ( D ) OTHER INFORMATION: /function="Intron 3"

( i x ) FEATURE:
    ( A ) NAME/KEY: exon
    ( B ) LOCATION: 1935..2081
    ( D ) OTHER INFORMATION: /product="Exon 4"

( i x ) FEATURE:
    ( A ) NAME/KEY: intron
    ( B ) LOCATION: 2082..3046
    ( D ) OTHER INFORMATION: /function="Intron 4"

( i x ) FEATURE:
    ( A ) NAME/KEY: exon
    ( B ) LOCATION: 3047..3180
    ( D ) OTHER INFORMATION: /product="Exon 5"

( i x ) FEATURE:
    ( A ) NAME/KEY: intron
    ( B ) LOCATION: 3181..3390
    ( D ) OTHER INFORMATION: /function="Intron 5"

( i x ) FEATURE:
    ( A ) NAME/KEY: exon
    ( B ) LOCATION: 3391..3563
    ( D ) OTHER INFORMATION: /product="Exon 6"

( i x ) FEATURE:
    ( A ) NAME/KEY: intron
    ( B ) LOCATION: 3564..4116
    ( D ) OTHER INFORMATION: /function="Intron 6"

( i x ) FEATURE:
    ( A ) NAME/KEY: exon
    ( B ) LOCATION: 4117..4354
    ( D ) OTHER INFORMATION: /product="Exon 7"

( i x ) FEATURE:
    ( A ) NAME/KEY: intron
    ( B ) LOCATION: 4355..5227
    ( D ) OTHER INFORMATION: /function="Intron 7"

( i x ) FEATURE:
    ( A ) NAME/KEY: exon
    ( B ) LOCATION: 5228..5452
    ( D ) OTHER INFORMATION: /product="Exon 8"

( i x ) FEATURE:

-continued (A) NAME/KEY: intron
                (B) LOCATION: 5453..5852
                (D) OTHER INFORMATION: /function="Intron 8"

(ix) FEATURE:
                (A) NAME/KEY: exon
                (B) LOCATION: 5853..6016
                (D) OTHER INFORMATION: /product="Exon 9"

(ix) FEATURE:
                (A) NAME/KEY: intron
                (B) LOCATION: 6017..6385
                (D) OTHER INFORMATION: /function="Intron 9"

(ix) FEATURE:
                (A) NAME/KEY: exon
                (B) LOCATION: 6386..6502
                (D) OTHER INFORMATION: /product="Exon 10"

(ix) FEATURE:
                (A) NAME/KEY: intron
                (B) LOCATION: 6503..6596
                (D) OTHER INFORMATION: /function="Intron 10"

(ix) FEATURE:
                (A) NAME/KEY: exon
                (B) LOCATION: 6597..7245
                (D) OTHER INFORMATION: /function="Exon 11"

(xi) SEQUENCE DESCRIPTION: SEQ ID NO:1:

```
GAGCTCTCCA TGCACACCTG TTACCGTTTC TGTCTTTATC TGTAAATATC TGTGTGTCTG      60
ACTTCCATGC CTCACACACC TCTATAGGGC AAAGACTGTC TTAAACATCT TGGTAGTGTC     120
AGTATTTTGC ACAGTGAAGT TTTTTTTTTT AAATTATATC AGCTTTATTT GTACCTTTTT     180
GACATTTCTA TCAAAAAGA AGTGTGCCTG CTGTGGTTCC CATCCTCTGG GATTTAGGAG      240
CCTCTACCCC ATTCTCCATG CAAATCTGTG TTCTAGGCTC TTCCTAAAGT TGTCACCCAT     300
ACATGCCCTC CAGAGTTTTA TAGGGCATAT AATCTGTAAC AGATGAGAGG AAGCCAATTG     360
CGCTTTAGAA ATATGGCTGT GATTGCCTCA CTTCCTGTGT CATGTGACGC TCCTAGTCAT     420
CACATGACCC ATCCACATCG GGAAGCCGGA ATTACTTGCA GGGCTAACCT AGTGCCTATA     480
GCTAAGGCAG GTACCTGCAT CCTTGTTTTT GTTTAGTGGA TCCTCTATCC TTCAGAGACT     540
CTGGAACCCC TGTGGTCTTC TCTTCATCTA ATGACCCTGA GGGGATGGAG TTTTCAAGTC     600
CTTCCAGAGA GGTAAGAGAG AGAGCTCCCA ATCAGCATTG TCACAGTGCT TCTGGAATCC     660
TGGCACTGGA ATTTAATGAA TGACAGACTC TCTTTGAATC CAGGGCCATC ATGGCTCTTT     720
GAGCAAGGCA CAGATGGAGG GAGGGGTCGA AGTTGAAATG GGTGGGAAGA GTGGTGGGGA     780
GCATCCTGAT TTGGGGTGGG CAGAGAGTTG TCATCAGAAG GGTTGCAGGG AGAGCTGCAC     840
CCAGGTTTCT GTGGGCCTTG TCCTAATGAA TGTGGGAGAC CGGGCCATGG GCACCCAAAG     900
GCAGCTAAGC CCTGCCCAGG AGAGTAGTTG AGGGGTGGAG AGGGGCTTGC TTTTCAGTCA     960
TTCCTCATTC TGTCCTCAGG AATGTCCCAA GCCTTTGAGT AGGGTAAGCA TCATGGCTGG    1020
CAGCCTCACA GGATTGCTTC TACTTCAGGC AGTGTCGTGG CATCAGGTG AGTGAGTCAA     1080
GGCAGTGGGG AGGTAGCACA GAGCCTCCCT TCTGCCTCAT AGTCCTTTGG TAGCCTTCCA    1140
GTAAGCTGGT GGTAGACTTT TAGTAGGTGC TCAATAAATC CTTTTGAGTG ACTGAGACCA    1200
ACTTTGGGGT GAGGATTTTG TTTTTTTTCT TTGAAACAG AGTCTTACTC TGTTGCCTGG     1260
GCTGGAGTGC AGTGGTGCAA TTTTGGCTCA TTCCAACCTC TGCCTCCCAG ATTCAAGCGA    1320
TTCTCTTGCT TCAGCTTCCC AGGTAGCTGG GATTACAGGC GGCCACCACT ACGCCCAGCT    1380
AATTTTTGTA TTTTTAGTAG AGACGGGGTT TCACCATGCT GGCAAGGCAG GTCTCAAACT    1440
CCTCACCTCA GGTGATCCGC CCACCTCGGC CTCCTAAAGT GCTAGGATTA CAGGTGTGAG    1500
CCCCTGCGCC CGGCCAAGGG GTGAGGAATT TTGAAACCGT GTTCAGTCTC TCCTAGCAGA    1560
```

```
TGTGTCCATT CTCCATGTCT TCATCAGACC TCACTCTGCT TGTACTCCCT CCCTCCCAGG  1620
TGCCCGCCCC TGCATCCCTA AAAGCTTCGG CTACAGCTCG GTGGTGTGTG TCTGCAATGC  1680
CACATACTGT GACTCCTTTG ACCCCCCGAC CTTTCCTGCC CTTGGTACCT TCAGCCGCTA  1740
TGAGAGTACA CGCAGTGGGC GACGGATGGA GCTGAGTATG GGCCCATCC AGGCTAATCA  1800
CACGGGCACA GGTAACCATT ACACCCCTCA CCCCTGGGC CAGGCTGGGT CCTCCTAGAG  1860
GTAAATGGTG TCAGTGATCA CCATGGAGTT TCCCGCTGGG TACTGATACC CTTATTCCCT  1920
GTGGATGTCC TCAGGCCTGC TACTGACCCT GCAGCCAGAA CAGAAGTTCC AGAAAGTGAA  1980
GGGATTTGGA GGGGCCATGA CAGATGCTGC TGCTCTCAAC ATCCTTGCCC TGTCACCCCC  2040
TGCCCAAAAT TTGCTACTTA AATCGTACTT CTCTGAAGAA GGTGAGGAGG AAGGGGACAA  2100
GATGACATAG AGCCATTGAA ACTTTTCATT TTTCTTTTCT TTTTTTAAAA TTTTTTTGAG  2160
GCAGAATCTC ACTCTGCCCA TTCTGTCGGC GAGACAGGAG TGCAGTGGTG TGATCTCCCC  2220
TCACAGCAAC CTCTGCCTCC CAGGCTATAG TGATTCTCCT GCCTCAGCCT CCTGAGTAGC  2280
TGGAATTATA GGCGTGCGCC ACTACCACCT GGCTAATTTT TGTATTTTA GTAGAGACAG  2340
GGTTTCATCA TGTTGACCAG GCTAGTCTTA AACTCCTGAC CTCAAATGAT ATACCTGCCT  2400
TGGCCTCCCG AAGTGCTGGA ATTACAAGTG TGAGCCACCG AGCCCAGCAG ACACTTTTCT  2460
TTTTTCTTTT TTTTTTTTG AGACAGAGTC TCGCACTGTC ACCCAGGCTG GAGTGCAGTG  2520
GCACAATCTC AGCTCACTGC AACCTCCACC TCCCGGGTTC AGGTGATTCT CCTGTCTCAG  2580
CCTCTCGAGT ACCTGGGATT ACAGGTGCCT GCCACCACGC CCGGCTAATT TTTTGTATTT  2640
TTAGTAGAGA CAGGGTTTCA CTATGTTGGC CAGGATGATT GCGAACTCCT GACCTCGTGA  2700
TCTGCCCACA TCGGCCTCCC AAAGTGCTGG GATTACATGC GTGAGCCACT GACACTTTTC  2760
TTTGCCCTTT CTTTGGACCC TGACTTCTGC CCATCCCTGA CATTTGGTTC CTGTTTTAAT  2820
GCCCTGTGAA ATAAGATTTC CCCGCCTATC ATCTGCTAAC TGCTACGGAC TCAGGCTCAG  2880
AAAGGCCTGC GCTTCACCCA GGTGCCAGCC TCCACAGGTT CCAACCCAGG AGCCCAAGTT  2940
CCCTTTGGCC CTGACTCAGA CACTATTAGG ACTGGCAAGT GATAAGCAGA GTCCCATACT  3000
CTCCTATTGA CTCGGACTAC CATATCTTGA TCATCCTTTT CTGTAGGAAT CGGATATAAC  3060
ATCATCCGGG TACCCATGGC CAGCTGTGAC TTCTCCATCC GCACCTACAC CTATGCAGAC  3120
ACCCCTGATG ATTTCCAGTT GCACAACTTC AGCCTCCCAG AGGAAGATAC CAAGCTCAAG  3180
GTAGGCATTC TAGCTTTTTC AGGCCCTGAG GGCCCTGATG TCTGGGGGTT GAGAAACTGT  3240
AGGGTAGGTC TGCTTGTACA GACATTTTGT CCCCTGCTGT TTTGTCCTGG GGTGGGAGG  3300
GTGGGGGCTA ATGGCTGAAC CGGATGCACT GGTTGGGCTA GTATGTGTTC CAACTCTGGG  3360
TGCTTCTCTC TTCACTACCT TTGTCTCTAG ATACCCCTGA TTCACCGAGC CCTGCAGTTG  3420
GCCCAGCGTC CCGTTTCACT CCTTGCCAGC CCTGGACAT CACCCACTTG GCTCAAGACC  3480
AATGGAGCGG TGAATGGGAA GGGGTCACTC AAGGGACAGC CCGGAGACAT CTACCACCAG  3540
ACCTGGGCCA GATACTTTGT GAAGTAAGGG ATCAGCAAGG ATGTGGGATC AGGACTGGCC  3600
TCCCATTTAG CCATGCTGAT CTGTGTCCCA ACCCTCAACC TAGTTCCACT TCCAGATCTG  3660
CCTGTCCTCA GCTCACCTTT CTACCTTCTG GGCCTTTCAG CCTTGGGCCT GTCAATCTTG  3720
CCCACTCCAT CAGGCTTCCT GTTCTCTCGG TCTGGCCCAC TTTCTTTTTA TTTTTCTTCT  3780
TTTTTTTTTT TTGAGAAGG AGTCTCTCTC TCTGTCACCC AGGCTGGAGT GCTGTGGCGC  3840
CATCTTCACT CACTGTAACC TTTGCCTCCT GAGTTCAAGC AATTCTCCTG CCTCAGCCTT  3900
CCAAGTAGCT GGGATATAGG CGCCTGCCAC CAGGCCCGGC TGATTTTTCT ATTTTTAGTA  3960
GAGACGGGGT TTCGCCAGGC TGTTCTCGAC TCCTGAACTC AAGTGATCCA CCTGCCTCGG  4020
```

```
CTTCCCAAAG TGCTGGGATT ACAGGTGTGA GCCACCACAC CCAGCTGGTC TGGTCCACTT    4080
TCTTGGCCGG ATCATTCATG ACCTTTCTCT TGCCAGGTTC CTGGATGCCT ATGCTGAGCA    4140
CAAGTTACAG TTCTGGGCAG TGACAGCTGA AAATGAGCCT TCTGCTGGGC TGTTGAGTGG    4200
ATACCCCTTC CAGTGCCTGG GCTTCACCCC TGAACATCAG CGAGACTTCA TTGCCCGTGA    4260
CCTAGGTCCT ACCCTCGCCA ACAGTACTCA CCACAATGTC CGCCTACTCA TGCTGGATGA    4320
CCAACGCTTG CTGCTGCCCC ACTGGGCAAA GGTGGTAAGG CCTGGACCTC CATGGTGCTC    4380
CAGTGACCTT CAAATCCAGC ATCCAAATGA CTGGCTCCCA AACTTAGAGC GATTTCTCTA    4440
CCCAACTATG GATTCCTAGA GCACCATTCC CCTGGACCTC CAGGGTGCCA TGGATCCCAC    4500
AGTTGTCGCT TGAAACCTTT CTAGGGGCTG GGCGAGGTGG CTCACTCATG CAAACCCAGC    4560
ACTTTGGGAA GCCGAGGCGG GTGATCACCT GAGGTCAGGA GTTAAGACC ACCCTGGCCA     4620
ACGTGTTGAA ACCCTGTGTC TACTAAAATA CAAAAAAAA AAATTATCTG GGCATGATGG     4680
TGGGTGTCTG TAATCCCAGC TACTCAGGAG GCTGAGAAGG GAGAATCAGT TGAACCCGGG    4740
AGATGGTGGT TGCGGTGAGC CGAGATCGCG CCACTGCACT CCAGCCTGGG AGGCTGAGCG    4800
AGACTCCATC TCGAAACCAA AACAAAACAA AACTATCTAG GCTGGGGGTG GTGGTTCATG    4860
TATGTATGTG TATATACATA TATATGTGTT TATATGGTAT ATATATATAC ACACACAC     4920
ATACATACAC ACACATACAC ACACAAATTA GCTGGGTGTG GCACCCGTGT AGTCCCAGCT    4980
ACTCAGGAGG CTAATGTGGG AGGATCAGTT GACCCTAGGA AGTCAAGGCT GCAGTGAGTC    5040
GTGATTGCGC CACTGTACTC CAGCCCGAGT GACAGAGTGA CATCCTGTCT CAAAAACAAA    5100
AAAAATCTC CCCAAACCTC TCTAGTTGCA TTCTTCCCGT CACCCACCTC CAGGATTCCT     5160
ACAACAGGAA CTAGAAGTTC CAGAAGCCTG TGTGCAAGGT CCAGGATCAG TTGCTCTTCC    5220
TTTGCAGGTA CTGACAGACC CAGAAGCAGC TAAATATGTT CATGGCATTG CTGTACATTG    5280
GTACCTGGAC TTTCTGGCTC CAGCCAAAGC CACCCTAGGG GAGACACACC GCCTGTTCCC    5340
CAACACCATG CTCTTTGCCT CAGAGGCCTG TGTGGGCTCC AAGTTCTGGG AGCAGAGTGT    5400
GCGGCTAGGC TCCTGGGATC GAGGGATGCA GTACAGCCAC AGCATCATCA CGGTAAGCCA    5460
CCCCAGTCTC CCTTCCTGCA AAGCAGACCT CAGACCTCTT ACTAGTTTCA CCAAAGACTG    5520
ACAGAAGCCC TTCCTGTCCA GCTTTCCCCA GCTAGCCTGC CCTTTTGAGC AACTCTGGGG    5580
AACCATGATT CCCTATCTTC CCTTTCCTTC ACAGGTCTGC ACACCTCATT GCCCCTTTTG    5640
CAACTACTGA GGCACTTGCA GCTGCCTCAG ACTTCTCAGC TCCCCTTGAG ATGCCTGGAT    5700
CTTCACACCC CCAACTCCTT AGCTACTAAG GAATGTGCCC CTCACAGGGC TGACCTACCC    5760
ACAGCTGCCT CTCCCACATG TGACCCTTAC CTACACTCTC TGGGGACCCC CAGTGTTGAG    5820
CCTTTGTCTC TTTGCCTTTG TCCTTACCCT AGAACCTCCT GTACCATGTG GTCGGCTGGA    5880
CCGACTGGAA CCTTGCCCTG AACCCCGAAG GAGGACCCAA TTGGGTGCGT AACTTTGTCG    5940
ACAGTCCCAT CATTGTAGAC ATCACCAAGG ACACGTTTTA CAAACAGCCC ATGTTCTACC    6000
ACCTTGGCCA CTTCAGGTGA GTGGAGGGCG GGCACCCCCA TTCCATACCA GGCCTATCAT    6060
CTCCTACATC GGATGGCTTA CATCACTCTA CACCACGAGG GAGCAGGAAG GTGTTCAGGG    6120
TGGAACCTCG GAAGAGGCAC ACCCATCCCC TTTTGCGCCA TGGAGGCAGG AAGTGACTAG    6180
GTAGCAACAG AAAACCCCAA TGCCTGAGGC TGGACTGCGA TGCAGAAAAG CAGGGTCAGT    6240
GCCCAGCAGC ATGGCTCCAG GCCTAGAGAG CCAGGGCAGA GCCTCTGCAG GAGTTATGGG    6300
GTGGGTCCGT GGGTGGGTGA CTTCTTAGAT GAGGGTTTCA TGGGAGGTAC CCCGAGGGAC    6360
TCTGACCATC TGTTCCCACA TTCAGCAAGT TCATTCCTGA GGGCTCCCAG AGAGTGGGGC    6420
TGGTTGCCAG TCAGAAGAAC GACCTGGACG CAGTGGCACT GATGCATCCC GATGGCTCTG    6480
```

| | | | | | | |
|---|---|---|---|---|---|---|
|CTGTTGTGGT|CGTGCTAAAC|CGGTGAGGGC|AATGGTGAGG|TCTGGGAAGT|GGGCTGAAGA|6540|
|CAGCGTTGGG|GGCCTTGGCA|GGATCACACT|CTCAGCTTCT|CCTCCCTGCT|CCCTAGCTCC|6600|
|TCTAAGGATG|TGCCTCTTAC|CATCAAGGAT|CCTGCTGTGG|GCTTCCTGGA|GACAATCTCA|6660|
|CCTGGCTACT|CCATTCACAC|CTACCTGTGG|CGTCGCCAGT|GATGGAGCAG|ATACTCAAGG|6720|
|AGGCACTGGG|CTCAGCCTGG|GCATTAAAGG|GACAGAGTCA|GCTCACACGC|TGTCTGTGAC|6780|
|TAAAGAGGGC|ACAGCAGGGC|CAGTGTGAGC|TTACAGCGAC|GTAAGCCCAG|GGGCAATGGT|6840|
|TTGGGTGACT|CACTTTCCCC|TCTAGGTGGT|GCCAGGGGCT|GGAGGCCCCT|AGAAAAAGAT|6900|
|CAGTAAGCCC|CAGTGTCCCC|CCAGCCCCCA|TGCTTATGTG|AACATGCGCT|GTGTGCTGCT|6960|
|TGCTTTGGAA|ACTGGGCCTG|GGTCCAGGCC|TAGGGTGAGC|TCACTGTCCG|TACAAACACA|7020|
|AGATCAGGGC|TGAGGGTAAG|GAAAAGAAGA|GACTAGGAAA|GCTGGGCCCA|AAACTGGAGA|7080|
|CTGTTTGTCT|TTCCTGGAGA|TGCAGAACTG|GGCCCGTGGA|GCAGCAGTGT|CAGCATCAGG|7140|
|GCGGAAGCCT|TAAAGCAGCA|GCGGGTGTGC|CCAGGCACCC|AGATGATTCC|TATGGCACCA|7200|
|GCCAGGAAAA|ATGGCAGCTC|TTAAAGGAGA|AAATGTTTGA|GCCCAGTCAG|TGTGAGTGGC|7260|
|TTTATTCTGG|GTGGCAGCAC|CCCGTGTCCG|GCTGTACCAA|CAACGAGGAG|GCACGGGGGC|7320|
|CTCTGGAATG|CATGAGAGTA|GAAAACCAG|TCTTGGGAGC|GTGAGGACAA|ATCATTCCTC|7380|
|TTCATCCTCC|TCAGCCATGC|CCAGGGTCCG|GGTGCCTGGG|GCCCGAGCAG|GCGTTGCCCG|7440|
|CTGGATGGAG|ACAATGCCGC|TGAGCAAGGC|GTAGCCACCA|TGGCTGCCAG|TCCTGCCAGC|7500|
|ACAGATAGGA|TCTGGTTCCG|GCGCCGGTAT|GGCTCCTCCT|CAGTCTCTGG|GCCTGCTGGT|7560|
|GTCTGGCGTT|GCGGTGGTAC|CTCAGCTGAG|GGTCAAGGAA|GGAAGGTGTG|TTAGGAGAAC|7620|

( 2 ) INFORMATION FOR SEQ ID NO:2:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: miscfeature
    ( B ) LOCATION: 57
    ( D ) OTHER INFORMATION: /note="N is either G in a normal
      glucocerebrosidase gene or N is GG in a mutant
      glucocerebrosidase gene"

( x i ) SEQUENCE DESCRIPTION: SEQ ID NO:2:

| | | | | | |
|---|---|---|---|---|---|
|GAATGTCCCA|AGCCTTTGAG|TAGGGTAAGC|ATCATGGCTG|GCAGCCTCAC|AGGATTNCTT|60|
|CTACTTCAGG|CAGTG| | | | |75|

( 2 ) INFORMATION FOR SEQ ID NO:3:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO (x i) SEQUENCE DESCRIPTION: SEQ ID NO:3:

GAATGTCCCA AGCCTTTGA                                                                 19

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:4:

CACTGCCTGA AGTAGATGC                                                                 19

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:5:

ACAGGATTGG CTTCTACT                                                                  18

(2) INFORMATION FOR SEQ ID NO:6:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:6:

GATTGGCATC                                                                           10

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:7:

CACTGCCTTG ACTCACTCAC                                                                20

(2) INFORMATION FOR SEQ ID NO:8:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

ACAGGATTGC TTCTACT 17

( 2 ) INFORMATION FOR SEQ ID NO:9:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

TACCCTAGAA CCTCCTG 17

( 2 ) INFORMATION FOR SEQ ID NO:10:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

TACCCTAGAG CCTCCTG 17

( 2 ) INFORMATION FOR SEQ ID NO:11:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

GAACGACCTG GACGCAG 17

( 2 ) INFORMATION FOR SEQ ID NO:12:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:12:

GAACGACCCG GACGCAG　　　　　　　　　　　　　　　　　　　　　　　　　　　　17

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:13:

TAAGCTCACA CTGGCCCTGC　　　　　　　　　　　　　　　　　　　　　　　　　　20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:14:

CTCTGGAACC CCTGTGGTCT　　　　　　　　　　　　　　　　　　　　　　　　　　20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:15:

CTCTTCATCT AATGACCCTG　　　　　　　　　　　　　　　　　　　　　　　　　　20

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:16:

CCAGTGCCTC CTTGAGTA          18

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:17:

CAAGGTCCAG GATCAGTTGC          20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:18:

AACGCTGTCT TCAGCCCACT          20

(2) INFORMATION FOR SEQ ID NO:19:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:19:

GAATGTCCCA AGCCTTTGAG TAGGGTAAGC ATCATGGCTG GCAGCCTCAC AGGATTGGCT          60

TCTACTTCAG GCAGTGTCGT GGGCATCAG          89